(12) United States Patent
Chodavarapu et al.

(10) Patent No.: US 10,695,744 B2
(45) Date of Patent: Jun. 30, 2020

(54) ADSORBENT BIPROCESSING CLARIFICATION AGENTS AND METHODS OF MAKING AND USING THE SAME

(71) Applicant: W. R. Grace & Co.-Conn., Columbia, MD (US)

(72) Inventors: Surya Kiran Chodavarapu, Ellicott City, MD (US); Feng Gu, Ellicott City, MD (US)

(73) Assignee: W. R. Grace & Co.-Conn., Columbia, MD (US)

( * ) Notice: Subject to any disclaimer, the term of this patent is extended or adjusted under 35 U.S.C. 154(b) by 111 days.

(21) Appl. No.: 15/579,876

(22) PCT Filed: Jun. 3, 2016

(86) PCT No.: PCT/US2016/035683
§ 371 (c)(1),
(2) Date: Dec. 5, 2017

(87) PCT Pub. No.: WO2016/196906
PCT Pub. Date: Dec. 8, 2016

(65) Prior Publication Data
US 2018/0169610 A1    Jun. 21, 2018

Related U.S. Application Data

(60) Provisional application No. 62/171,669, filed on Jun. 5, 2015.

(51) Int. Cl.
| | | |
|---|---|---|
| B01J 20/10 | (2006.01) | |
| B01D 15/08 | (2006.01) | |
| C07K 1/14 | (2006.01) | |
| B01J 20/32 | (2006.01) | |
| B01J 20/28 | (2006.01) | |
| B01J 20/26 | (2006.01) | |
| B01J 20/30 | (2006.01) | |
| B01D 15/12 | (2006.01) | |

(52) U.S. Cl.
CPC .......... *B01J 20/103* (2013.01); *B01D 15/08* (2013.01); *B01J 20/262* (2013.01); *B01J 20/28004* (2013.01); *B01J 20/28016* (2013.01); *B01J 20/28057* (2013.01); *B01J 20/28061* (2013.01); *B01J 20/28069* (2013.01); *B01J 20/28078* (2013.01); *B01J 20/28088* (2013.01); *B01J 20/3042* (2013.01); *B01J 20/3204* (2013.01); *B01J 20/327* (2013.01); *B01J 20/3219* (2013.01); *B01J 20/3272* (2013.01); *B01J 20/3276* (2013.01); *C07K 1/14* (2013.01); *B01D 15/125* (2013.01); *B01J 2220/46* (2013.01)

(58) Field of Classification Search
CPC .......... F02B 23/101; F02B 23/0696; F02B 23/0669; F02B 23/063; F02B 23/0618; F02B 2023/102; F02B 2023/085; F02D 37/02; F02D 41/401; F02D 41/3041; F02D 2700/10; F02D 2041/389; F02P 15/08; F02F 3/28; F02F 3/26; Y02T 10/125; Y02T 10/44
See application file for complete search history.

(56) References Cited

U.S. PATENT DOCUMENTS

| | | |
|---|---|---|
| 3,505,785 A | 4/1970 | Kirkland |
| 3,526,603 A | 9/1970 | Acker ................ B01J 11/36 |
| 3,652,216 A | 3/1972 | Krekeler et al. ............. 23/162 |
| 3,782,075 A | 1/1974 | Kirkland ..................... 55/67 |
| 3,855,172 A | 12/1974 | Iler et al. .................. 260/39 R |
| 3,869,409 A | 3/1975 | Bebris et al. ............... 262/446 |
| 3,888,972 A | 6/1975 | Kiselev et al. ............. 423/338 |
| 3,904,598 A | 9/1975 | Isaac ....................... 260/210.5 |
| 3,943,072 A | 3/1976 | Thomson et al. ........ 252/455 R |
| 3,956,179 A | 5/1976 | Sebastian et al. ........... 252/430 |
| 3,975,293 A | 8/1976 | LePage ..................... 252/317 |
| 3,984,349 A | 10/1976 | Meiler et al. .............. 252/428 |
| 4,010,242 A | 3/1977 | Iler et al. .................. 423/335 |
| 4,029,583 A | 6/1977 | Ho Chang et al. .......... 252/184 |
| 4,034,139 A | 7/1977 | Mazarguil et al. .......... 428/405 |
| 4,061,828 A | 12/1977 | Mazarguil et al. .......... 428/403 |
| 4,070,286 A | 1/1978 | Iler et al. ................. 210/31 C |
| 4,076,651 A | 2/1978 | Jacques ..................... 252/451 |
| 4,100,149 A | 7/1978 | Meiler et al. ............. 260/112 R |
| 4,104,363 A | 8/1978 | Vozka et al. ............... 423/338 |
| 4,118,316 A | 10/1978 | Talley et al. ............. 210/31 C |
| 4,124,699 A | 11/1978 | Michel et al. .............. 423/628 |
| 4,131,542 A | 12/1978 | Bergna et al. .............. 210/31 |
| 4,140,653 A | 2/1979 | Shirichi et al. ............ 252/430 |
| 4,157,920 A | 6/1979 | Wason et al. ............... 106/292 |
| 4,168,216 A | 9/1979 | Burkhardt et al. ........... 204/98 |

(Continued)

FOREIGN PATENT DOCUMENTS

| | | |
|---|---|---|
| CA | 1303594 C | 6/1992 |
| CA | 2564413 A1 | 12/2005 |

(Continued)

OTHER PUBLICATIONS

Azizi, Najmodin; Saidi, Mohammad, "Highly Chemoselective Addition of Amines to Epoxides in Water", Organic Letters, v 7, n 17, p. 3649-3651 (2005).

Buncek, M.; Backovska, V.; Holasova, S.; Radilova, H.; Safarova, M.; Kunc, F.; Haluza, R., "Unusual Chromatographic Behavior of Oligonucleotide Sequence Isomers on Two Different Anion Exchange HPLC Columns", Analytical Biochemistry, n 348, p. 300-306 (2006).

Chen, Feng; Wan, Decheng; Chang, Zhihong; Pu, Hongting; Jin, Ming, "Highly Efficient Separation, Enrichment, and Recovery of Peptides by Silica-Supported Polyethylenimine", Langmuir, n 30, p. 12250-12257 (2014).

Dib, Samia; Faria, Anizio, "Polyethyleneimine Immobilized on Silica Endcapped with Octadecyl Groups as a Stationary Phase for RP-LC", Chromatographia, n 77, p. 533-541 (2014).

(Continued)

*Primary Examiner* — Anthony J Zimmer

(57) ABSTRACT

Adsorbent clarification agents suitable for use in bioprocessing procedures are disclosed. Methods of making and using the adsorbent clarification agents are also disclosed.

29 Claims, 1 Drawing Sheet

(56) References Cited

U.S. PATENT DOCUMENTS

| | | | |
|---|---|---|---|
| 4,170,685 A | 10/1979 | Rembaum et al. ............ 428/402 |
| 4,199,450 A | 4/1980 | Dulout et al. .................. 210/31 |
| 4,229,342 A | 10/1980 | Mirabel ........................ 230/120 |
| 4,275,300 A | 6/1981 | Abbott ........................ 250/304 |
| 4,298,500 A | 11/1981 | Abbott ........................ 252/428 |
| 4,308,254 A | 12/1981 | Tayot et al. ................... 424/124 |
| 4,322,542 A | 3/1982 | Abbott ........................ 556/425 |
| 4,329,434 A | 5/1982 | Kimoto et al. ............... 521/27 |
| 4,329,435 A | 5/1982 | Kimoto et al. ............... 521/38 |
| 4,376,140 A | 3/1983 | Kimoto et al. ............... 427/244 |
| 4,397,827 A | 8/1983 | Chu ............................ 423/326 |
| 4,415,631 A | 11/1983 | Schutijser |
| 4,469,630 A | 9/1984 | Flashner |
| 4,496,461 A | 1/1985 | Leeke et al. .................. 210/198.2 |
| 4,517,131 A | 5/1985 | Hefner, Jr. ................... 260/465 F |
| 4,532,232 A | 7/1985 | Larsson et al. |
| 4,536,352 A | 8/1985 | Kimoto et al. ............... 260/543 |
| 4,540,486 A | 9/1985 | Ramsden .................... 210/198.2 |
| 4,551,245 A | 11/1985 | Ramsden et al. ............. 210/198.2 |
| 4,560,704 A | 12/1985 | Regnier et al. |
| 4,569,917 A | 2/1986 | Maier et al. ................... 436/71 |
| 4,576,927 A | 3/1986 | Kuroda et al. |
| 4,581,428 A | 4/1986 | Farnham et al. ............. 526/190 |
| 4,596,660 A | 6/1986 | Hou |
| 4,597,913 A | 7/1986 | Kimoto et al. ............... 658/436 |
| 4,606,825 A | 8/1986 | Crane et al. .................. 210/635 |
| 4,639,513 A | 1/1987 | Hou et al. .................... 530/387 |
| 4,640,909 A | 2/1987 | Ramsden et al. ............. 502/407 |
| 4,648,975 A | 3/1987 | Barkatt et al. ............... 210/656 |
| 4,650,784 A | 3/1987 | Ramsden et al. ............. 502/407 |
| 4,661,248 A | 4/1987 | Ramsden et al. ............. 210/198.2 |
| 4,673,734 A | 6/1987 | Tayot et al. ................... 530/364 |
| 4,676,898 A | 6/1987 | Saxena ........................ 210/198.2 |
| 4,699,717 A | 10/1987 | Riesner et al. ............... 21/635 |
| 4,704,374 A | 11/1987 | Jacques ....................... 502/8 |
| 4,724,207 A | 2/1988 | Hou et al. .................... 435/180 |
| 4,724,210 A | 2/1988 | Oka et al. .................... 436/238 |
| 4,732,887 A | 3/1988 | Obanawa et al. ............ 502/402 |
| 4,740,298 A | 4/1988 | Andresen et al. ........... 210/198.3 |
| 4,745,097 A | 5/1988 | Maekawa et al. ............ 503/209 |
| 4,746,572 A | 5/1988 | Glajch et al. ................ 428/403 |
| 4,756,834 A | 7/1988 | Muller et al. ................ 210/635 |
| 4,780,423 A | 10/1988 | Bluestein et al. ............ 436/527 |
| 4,783,264 A | 11/1988 | Nylen et al. .................. 210/638 |
| 4,851,382 A | 7/1989 | Kusano et al. ............... 502/401 |
| 4,855,054 A | 8/1989 | Williams ..................... 210/635 |
| 4,895,806 A | 1/1990 | Le et al. ...................... 435/288 |
| 4,917,781 A | 4/1990 | Sharifian et al. ............. 204/72 |
| 4,923,978 A | 5/1990 | McCormick ................. 536/27 |
| 4,950,634 A | 8/1990 | Williams et al. ............. 502/407 |
| 4,956,180 A | 9/1990 | Cassani et al. ............... 424/118 |
| 4,959,340 A | 9/1990 | Williams ..................... B01J 20/22 |
| 4,990,456 A | 2/1991 | Loucks et al. ............... 436/139 |
| 5,004,688 A | 4/1991 | Craig et al. ................... 436/59.3 |
| 5,009,688 A | 4/1991 | Nakanishi .................... 86/18.3 |
| 5,030,286 A | 7/1991 | Crawford et al. ............ 106/435 |
| 5,032,266 A | 7/1991 | Kirkland et al. ............. 210/196.2 |
| 5,035,803 A | 7/1991 | Cohen ......................... 210/656 |
| 5,057,426 A | 10/1991 | Henco et al. ................. 435/270 |
| 5,059,654 A | 10/1991 | Hou et al. |
| 5,085,779 A | 2/1992 | Crane et al. .................. 210/635 |
| 5,087,359 A | 2/1992 | Kakodkar et al. ........... 210/198.2 |
| 5,091,433 A | 2/1992 | Wulff et al. .................. 521/54 |
| 5,092,992 A | 3/1992 | Crane et al. .................. 210/196.2 |
| 5,099,923 A | 3/1992 | Aften et al. .................. 166/294 |
| 5,128,291 A | 7/1992 | Wax et al. .................... 502/8 |
| 5,141,806 A | 8/1992 | Koontz ........................ 428/316.5 |
| 5,149,425 A | 9/1992 | Mazid .......................... 210/198.2 |
| 5,149,553 A | 9/1992 | Berg ............................ 426/330.4 |
| 5,149,646 A | 9/1992 | Crane et al. |
| 5,151,350 A | 9/1992 | Colbert et al. ............... 435/89.1 |
| 5,152,906 A | 10/1992 | Aften et al. .................. 252/8.551 |
| 5,190,660 A | 3/1993 | Lindoy et al. ................ 210/670 |
| 5,190,844 A | 3/1993 | Yabuuchi et al. ............ 430/137 |
| 5,203,991 A | 4/1993 | Kutsuna et al. .............. 210/198.2 |
| 5,230,833 A | 7/1993 | Romberger et al. ........ 252/363.5 |
| 5,268,097 A | 12/1993 | Girot et al. ................... 502/402 |
| 5,318,848 A | 6/1994 | Itoh et al. ..................... 428/405 |
| 5,354,548 A | 10/1994 | Araya et al. .................. 423/700 |
| 5,372,820 A | 12/1994 | Jozefonvicz nee Dorgebray et al. ............................ 424/499 |
| 5,380,706 A | 1/1995 | Himes et al. ................. 507/129 |
| 5,401,809 A | 3/1995 | Gitzel et al. .................. 525/337 |
| 5,431,807 A | 7/1995 | Frechet et al. ............... 210/198.2 |
| 5,447,859 A | 9/1995 | Prussak ........................ 435/239 |
| 5,451,660 A | 9/1995 | Builder et al. ................ 530/344 |
| 5,453,186 A | 9/1995 | Muller et al. ................ 210/198.2 |
| 5,468,847 A | 11/1995 | Heilmann et al. ............ 530/413 |
| 5,480,542 A | 1/1996 | Asakawa et al. ............. 210/198.2 |
| 5,510,394 A | 4/1996 | Hodgdon ..................... 521/27 |
| 5,512,169 A | 4/1996 | Williams ..................... 210/198.2 |
| 5,593,576 A | 1/1997 | Girot et al. ................... 210/198.2 |
| 5,593,757 A | 1/1997 | Kashiwazaki et al. ...... 428/195 |
| 5,610,274 A | 3/1997 | Wong ........................... 530/334 |
| 5,622,743 A | 4/1997 | Tanaka et al. |
| 5,624,875 A | 4/1997 | Nakanishi et al. ........... 501/39 |
| 5,633,290 A | 5/1997 | Frechet et al. ............... 521/54 |
| 5,652,348 A | 7/1997 | Burton et al. ................ 536/20 |
| 5,674,932 A | 10/1997 | Agostini et al. ............. 524/430 |
| 5,701,956 A | 12/1997 | Hardy et al. .................. 166/295 |
| 5,707,516 A | 1/1998 | Tomizawa et al. .......... 210/198.2 |
| 5,710,264 A | 1/1998 | Urdea et al. .................. 536/23.1 |
| 5,731,186 A | 3/1998 | McCaman et al. |
| 5,759,405 A | 6/1998 | Anderson et al. ........... 210/656 |
| 5,805,264 A | 9/1998 | Janssen et al. ............... 351/160 R |
| 5,808,041 A | 9/1998 | Padhye et al. ................ 536/25.4 |
| 5,856,379 A | 1/1999 | Shiratsuchi et al. |
| 5,861,134 A | 1/1999 | Swanson ...................... 423/335 |
| 5,888,397 A | 3/1999 | Rogers et al. ................ 210/634 |
| 5,904,848 A | 5/1999 | Wong et al. .................. 210/500.36 |
| 5,906,747 A | 5/1999 | Coffman et al. ............. 210/635 |
| 5,911,963 A | 6/1999 | Krivak et al. ................ 423/335 |
| 5,912,037 A | 6/1999 | Michos |
| 5,914,044 A | 6/1999 | Lindoy et al. ................ 210/670 |
| 5,922,449 A | 7/1999 | Revis .......................... 428/306.6 |
| 5,922,531 A | 7/1999 | Dubin et al. |
| 5,945,525 A | 8/1999 | Uematsu et al. ............. 536/25.42 |
| 5,948,894 A | 9/1999 | Berry et al. .................. 538/391.1 |
| 5,968,652 A | 10/1999 | Hanaggi et al. .............. 428/405 |
| 5,970,915 A | 10/1999 | Schlueter et al. ............ 119/171 |
| 5,973,068 A | 10/1999 | Yamaya et al. |
| 5,976,479 A | 11/1999 | Alcaraz et al. ............... 423/335 |
| 5,993,935 A | 11/1999 | Rasmussen et al. |
| 6,027,945 A | 2/2000 | Smith et al. .................. 436/526 |
| 6,037,465 A | 3/2000 | Hillebrand et al. .......... 535/25.42 |
| 6,043,354 A | 3/2000 | Hillebrand et al. .......... 536/25.42 |
| 6,074,555 A | 6/2000 | Boos et al. ................... 210/198.2 |
| 6,090,288 A | 7/2000 | Berglund et al. |
| 6,127,526 A | 10/2000 | Blank ........................... 530/413 |
| 6,168,773 B1 | 1/2001 | Sharp ........................... 423/338 |
| 6,171,486 B1 | 1/2001 | Green et al. .................. 210/198.2 |
| 6,204,306 B1 | 3/2001 | Chabrecek et al. .......... 523/106 |
| 6,248,911 B1 | 6/2001 | Canessa et al. .............. 554/191 |
| 6,284,470 B1 | 9/2001 | Bitner et al. .................. 435/6 |
| 6,310,199 B1 | 10/2001 | Smith et al. .................. 536/25.4 |
| 6,355,726 B1 | 3/2002 | Doemling et al. ........... 525/64.1 |
| 6,362,320 B1 | 3/2002 | Park et al. .................... 530/412 |
| 6,372,353 B2 | 4/2002 | Karger et al. ................ 428/447 |
| 6,376,194 B2 | 4/2002 | Smith et al. .................. 435/8 |
| 6,379,500 B2 | 4/2002 | Greenwood et al. ........ 162/181.6 |
| 6,383,990 B1 | 5/2002 | Dawson et al. .............. 507/209 |
| 6,387,974 B1 | 5/2002 | Deissler et al. .............. 521/150 |
| 6,426,315 B1 | 7/2002 | Bergstrom et al. |
| 6,428,707 B1 | 8/2002 | Berg et al. .................... 210/661 |
| 6,435,012 B2 | 8/2002 | Maikner ...................... 73/61.52 |
| 6,472,486 B2 | 10/2002 | Klaerner et al. ............. 526/220 |
| 6,482,324 B2 | 11/2002 | Kirkland et al. ............. 210/656 |
| 6,488,855 B2 | 12/2002 | Gjerde et al. ................ 210/635 |
| 6,497,964 B1 | 12/2002 | Matsumura et al. ......... 428/447 |
| 6,512,060 B1 | 1/2003 | Matyjaszewski et al. .... 526/111 |
| 6,537,793 B2 | 3/2003 | Blanche et al. .............. 435/239 |
| 6,555,151 B2 | 4/2003 | Hu et al. ....................... 426/422 |
| 6,565,905 B1 | 5/2003 | Ito et al. ....................... 426/330.4 |
| 6,569,910 B1 | 5/2003 | Spindler et al. .............. 521/30 |

(56) References Cited

U.S. PATENT DOCUMENTS

| | | | |
|---|---|---|---|
| 6,596,843 B2 | 7/2003 | Brunelle et al. | 528/486 |
| 6,620,326 B1 | 9/2003 | Lihme et al. | 210/635 |
| 6,624,205 B2 | 9/2003 | Muranaka | 521/25 |
| 6,632,848 B2 | 10/2003 | Sugaya | 521/27 |
| 6,649,572 B2 | 11/2003 | Dawson et al. | 507/209 |
| 6,797,814 B2 | 9/2004 | Blank | 530/413 |
| 6,802,966 B2 | 10/2004 | Wormsbecher | 210/198.2 |
| 6,818,259 B1 | 11/2004 | Koontz | 427/562 |
| 6,852,009 B2 | 2/2005 | Kawase et al. | 431/36 |
| 6,861,103 B2 | 3/2005 | Chang et al. | 427/522 |
| 6,911,192 B2 | 6/2005 | Nakanishi | 423/338 |
| 6,916,536 B1 | 7/2005 | Hammen et al. | 428/407 |
| 6,949,613 B2 | 9/2005 | Haddleton | 526/90 |
| 6,972,090 B2 | 12/2005 | Boschetti et al. | 210/198.2 |
| 6,994,791 B2 | 2/2006 | Muller et al. | 210/656 |
| 6,994,964 B1 | 2/2006 | Chang et al. | 435/6 |
| 6,998,040 B2 | 2/2006 | Malik et al. | 210/198.2 |
| 6,998,042 B2 | 2/2006 | Wormsbecher | 210/198.2 |
| 7,008,542 B2 | 3/2006 | Belew | |
| 7,012,044 B2 | 3/2006 | Dawson et al. | 507/211 |
| 7,015,281 B2 | 3/2006 | Britsch et al. | 525/61 |
| 7,033,505 B2 | 4/2006 | Urano | 210/656 |
| 7,067,059 B2 | 6/2006 | Maloisel et al. | 210/635 |
| 7,074,491 B2 | 7/2006 | Liu et al. | 428/447 |
| 7,078,224 B1 | 7/2006 | Bitner et al. | 435/270 |
| 7,125,488 B2 | 10/2006 | Li | 210/198.2 |
| 7,128,884 B2 | 10/2006 | Kirkland et al. | 423/335 |
| 7,166,213 B2 | 1/2007 | Wormsbecher | 210/198.2 |
| 7,192,560 B2 | 3/2007 | Parthasarathy et al. | 422/101 |
| 7,198,855 B2 | 4/2007 | Liebmann-Vinson et al. | 428/447 |
| 7,220,703 B2 | 5/2007 | Hammen et al. | 502/406 |
| 7,229,655 B2 | 6/2007 | Hu et al. | 426/422 |
| 7,244,568 B2 | 7/2007 | Goldsborough | |
| 7,250,214 B2 | 7/2007 | Walter et al. | 428/405 |
| 7,250,253 B1 | 7/2007 | Klapproth et al. | 435/6 |
| 7,316,919 B2 | 1/2008 | Childs et al. | 435/177 |
| 7,318,900 B2 | 1/2008 | DeMarco | 210/656 |
| 7,323,347 B2 | 1/2008 | Quinn | 436/518 |
| 7,329,386 B2 | 2/2008 | Kobayashi et al. | 422/70 |
| 7,332,327 B2 | 2/2008 | Vikholm et al. | 435/287.2 |
| 7,338,768 B1 | 3/2008 | Trau et al. | 435/7.1 |
| 7,374,684 B2 | 5/2008 | Gibson et al. | 210/836 |
| 7,375,168 B2 | 5/2008 | Zhang et al. | 525/474 |
| 7,378,479 B2 | 5/2008 | Tamareselvy et al. | 526/333 |
| 7,390,403 B2 | 6/2008 | Siwak | 210/198.2 |
| 7,396,561 B2 | 7/2008 | Ruhe | 427/214 |
| 7,456,276 B2 | 11/2008 | Christensen et al. | 536/123.1 |
| 7,476,474 B2 | 1/2009 | Ganguli et al. | 430/5 |
| 7,479,223 B2 | 1/2009 | DiLeo et al. | 210/198.2 |
| 7,482,169 B2 | 1/2009 | Gjerde et al. | 436/178 |
| 7,534,623 B2 | 5/2009 | Landers et al. | 436/177 |
| 7,560,258 B2 | 7/2009 | Brueggemeier et al. | 435/174 |
| 7,608,234 B2 | 10/2009 | Stenzel et al. | 423/335 |
| 7,671,203 B2 | 3/2010 | Antonini | 546/44 |
| 7,674,835 B2 | 3/2010 | Rasmussen et al. | 521/31 |
| 7,683,011 B2 | 3/2010 | Putzig | 507/273 |
| 7,692,013 B2 | 4/2010 | Antonini | |
| 7,714,112 B2 | 5/2010 | Engstrand et al. | 530/390.5 |
| 7,732,383 B2 | 6/2010 | Putzig | 507/271 |
| 7,736,612 B2 | 6/2010 | Kubota | 423/335 |
| 7,745,582 B2 | 6/2010 | Lihme et al. | 530/387.1 |
| 7,754,660 B2 | 7/2010 | Putzig | 507/271 |
| RE41,595 E | 8/2010 | Shandle et al. | 210/635 |
| 7,767,399 B2 | 8/2010 | Murphy et al. | |
| 7,780,946 B2 | 8/2010 | Wormsbecher | 423/659 |
| 7,790,657 B2 | 9/2010 | Putzig | 507/273 |
| 7,795,189 B2 | 9/2010 | Putzig | 507/273 |
| 7,795,190 B2 | 9/2010 | Putzig | 507/273 |
| 7,824,548 B2 | 11/2010 | DiLeo | 210/198.2 |
| 7,851,417 B2 | 12/2010 | Putzig | 507/271 |
| 7,867,738 B2 | 1/2011 | Dicosimo et al. | |
| 7,875,317 B2 | 1/2011 | Nakagawa et al. | 427/387 |
| 7,897,051 B2 | 3/2011 | Sohling et al. | 210/670 |
| 7,919,177 B2 | 4/2011 | Jiang et al. | 428/304.4 |
| 7,922,908 B2 | 4/2011 | Allington et al. | 210/635 |
| 7,943,046 B2 | 5/2011 | Martosella et al. | 210/635 |
| 7,960,311 B2 | 6/2011 | Carlson | 506/13 |
| 7,994,092 B2 | 8/2011 | Gorkovenko et al. | 502/404 |
| 8,197,782 B2 | 6/2012 | DeVera | 423/339 |
| 8,242,050 B2 | 8/2012 | Lu et al. | 502/407 |
| 8,481,298 B2 | 7/2013 | Andersson et al. | 435/239 |
| 8,551,894 B2 | 10/2013 | Seshadri et al. | 442/63 |
| 8,658,277 B2 | 2/2014 | Wyndham et al. | |
| 8,673,988 B2 | 3/2014 | Graalfs et al. | 521/32 |
| 8,791,220 B2 | 7/2014 | Jiang et al. | |
| 9,556,258 B2 * | 1/2017 | Nti-Gyabaah | C07K 1/36 |
| 2002/0006493 A1 | 1/2002 | Chabrecek et al. | 428/64.1 |
| 2002/0012982 A1 | 1/2002 | Blakesley et al. | 435/183 |
| 2002/0028520 A1 | 3/2002 | Boschetti et al. | 436/518 |
| 2002/0043499 A1 | 4/2002 | Hammen et al. | 210/656 |
| 2002/0099104 A1 | 7/2002 | Muranaka et al. | |
| 2002/0127587 A1 | 9/2002 | Simms et al. | 435/6 |
| 2002/0166816 A1 | 11/2002 | Allen et al. | 210/556 |
| 2003/0017464 A1 | 1/2003 | Pohl | 435/6 |
| 2003/0075508 A1 | 4/2003 | Woodruff et al. | 210/683 |
| 2003/0108879 A1 | 6/2003 | Klaerner et al. | 435/6 |
| 2003/0171443 A1 | 9/2003 | Erbacher | 521/27 |
| 2003/0187227 A1 | 10/2003 | Lihme et al. | 530/367.1 |
| 2003/0201229 A1 | 10/2003 | Siwak et al. | 210/650 |
| 2003/0225261 A1 | 12/2003 | Taylor et al. | 535/25.5 |
| 2004/0028901 A1 | 2/2004 | Rumpf et al. | 428/375 |
| 2004/0053355 A1 | 3/2004 | Wainer | |
| 2004/0058059 A1 | 3/2004 | Linford et al. | 427/58 |
| 2004/0091411 A1 | 5/2004 | Modrek-Najafabadi | 423/338 |
| 2004/0127648 A1 | 7/2004 | Guerrer et al. | 525/227 |
| 2004/0159611 A1 | 8/2004 | Urano | 210/656 |
| 2004/0203308 A1 | 10/2004 | Ko et al. | |
| 2004/0211724 A1 | 10/2004 | Gibson et al. | 210/638 |
| 2004/0224843 A1 | 11/2004 | Hammen et al. | 502/402 |
| 2004/0266896 A1 | 12/2004 | Britsch et al. | 521/38 |
| 2005/0029196 A1 | 2/2005 | Rhemrev-Boom | 210/656 |
| 2005/0032922 A1 * | 2/2005 | Deorkar | B01D 15/362 521/31 |
| 2005/0100905 A1 | 5/2005 | Nassoy et al. | 435/6 |
| 2005/0106602 A1 | 5/2005 | Akhavan-Tafti | 435/6 |
| 2005/0115903 A1 | 6/2005 | Hallier-Soulier et al. | 210/656 |
| 2005/0158837 A1 | 7/2005 | Bond | |
| 2005/0200025 A1 | 9/2005 | Casey et al. | 257/762 |
| 2005/0269257 A1 | 12/2005 | Voute et al. | 210/502.1 |
| 2005/0282294 A1 | 12/2005 | Britsch | 436/514 |
| 2006/0035224 A1 | 2/2006 | Johansen | |
| 2006/0041035 A1 | 2/2006 | Poppe et al. | 523/200 |
| 2006/0058181 A1 | 3/2006 | Margetts | 502/159 |
| 2006/0105391 A1 | 5/2006 | Engel et al. | 435/7.1 |
| 2006/0120683 A1 | 6/2006 | Kamp et al. | 385/141 |
| 2006/0144770 A1 | 7/2006 | Granger et al. | 210/198.2 |
| 2006/0147344 A1 | 7/2006 | Ahn et al. | 422/70 |
| 2006/0180549 A1 | 8/2006 | Liu et al. | 210/556 |
| 2006/0240633 A1 | 10/2006 | Martosella et al. | 438/348 |
| 2007/0112178 A1 | 5/2007 | Johansson et al. | 530/387.1 |
| 2007/0135304 A1 | 6/2007 | Walter et al. | |
| 2007/0141325 A1 | 6/2007 | O'Gara et al. | 428/332 |
| 2007/0178465 A1 | 8/2007 | Sudor et al. | 435/6 |
| 2007/0181482 A1 | 8/2007 | Abudokirim et al. | 210/312.6 |
| 2007/0193954 A1 | 8/2007 | Busson | 210/656 |
| 2007/0215547 A1 | 9/2007 | O'Gara | 210/656 |
| 2007/0276131 A1 | 11/2007 | Ferre et al. | 530/420 |
| 2008/0017579 A1 | 1/2008 | Hermansson et al. | 210/656 |
| 2008/0025900 A1 | 1/2008 | Mori | 423/335 |
| 2008/0026486 A1 | 1/2008 | Cooper et al. | 436/518 |
| 2008/0033103 A1 | 2/2008 | Kameda et al. | 524/571 |
| 2008/0038750 A1 | 2/2008 | Piehler et al. | 435/7.1 |
| 2008/0053908 A1 | 3/2008 | Chordia et al. | 210/656 |
| 2008/0071003 A1 | 3/2008 | Sellergren et al. | |
| 2008/0116122 A1 | 5/2008 | Wheelwright et al. | 210/87 |
| 2008/0146454 A1 | 6/2008 | Cuppoletti et al. | 506/6 |
| 2008/0153100 A1 | 6/2008 | Rank et al. | 435/6 |
| 2008/0154029 A1 | 6/2008 | Balayan et al. | 536/25.4 |
| 2008/0164211 A1 | 7/2008 | Lindner et al. | |
| 2008/0210615 A1 | 9/2008 | Joehnck et al. | 210/198.2 |
| 2008/0213906 A1 | 9/2008 | Aurand et al. | 436/83 |
| 2008/0223794 A1 | 9/2008 | Yamamichi et al. | 210/767 |
| 2008/0236824 A1 | 10/2008 | Putzig | 166/280.1 |

(56) References Cited

U.S. PATENT DOCUMENTS

| | | | |
|---|---|---|---|
| 2008/0249326 A1 | 10/2008 | Nakajima et al. | 556/410 |
| 2008/0269368 A1 | 10/2008 | Wyndham et al. | 521/164 |
| 2008/0269475 A1 | 10/2008 | Sohling | 536/25.4 |
| 2008/0277346 A1 | 11/2008 | Kirkland et al. | 210/656 |
| 2008/0293959 A1 | 11/2008 | Liu et al. | 556/449 |
| 2008/0311681 A1 | 12/2008 | Johannsen et al. | 436/548 |
| 2009/0035876 A1 | 2/2009 | Williams et al. | 436/529 |
| 2009/0048433 A1 | 2/2009 | Richter et al. | |
| 2009/0048439 A1 | 2/2009 | Weisburg et al. | 536/25.41 |
| 2009/0056541 A1 | 3/2009 | Davison et al. | 95/86 |
| 2009/0062519 A1 | 3/2009 | Okamoto et al. | 536/20 |
| 2009/0074709 A1 | 3/2009 | Koepsel et al. | 424/78.32 |
| 2009/0127501 A1 | 5/2009 | Kashima et al. | 252/79.5 |
| 2009/0151946 A1 | 6/2009 | Putzig | 166/280.2 |
| 2009/0151947 A1 | 6/2009 | Putzig | 166/280.2 |
| 2009/0170973 A1 | 7/2009 | Mattiasson et al. | 521/134 |
| 2009/0186093 A1 | 7/2009 | Liu et al. | 424/497 |
| 2009/0192342 A1 | 7/2009 | Coupard et al. | 685/533 |
| 2009/0197332 A1 | 8/2009 | Andreou et al. | 435/375 |
| 2009/0206034 A1 | 8/2009 | Nakajima | 210/635 |
| 2009/0211453 A1 | 8/2009 | Nassivera et al. | 96/153 |
| 2009/0221809 A1 | 9/2009 | Sohling et al. | 536/25.4 |
| 2009/0232950 A1 | 9/2009 | Brothers, Jr. et al. | |
| 2009/0246885 A1 | 10/2009 | Bian et al. | 436/501 |
| 2009/0277838 A1 | 11/2009 | Liu et al. | 210/656 |
| 2009/0294362 A1 | 12/2009 | Persson et al. | 210/656 |
| 2009/0297853 A1 | 12/2009 | Kirkland et al. | 428/403 |
| 2009/0306292 A1 | 12/2009 | Bendejacq et al. | 525/55 |
| 2009/0308599 A1 | 12/2009 | Dusterhoft et al. | 166/249 |
| 2009/0308811 A1 | 12/2009 | Tepper et al. | 210/656 |
| 2010/0022419 A1 | 1/2010 | Reed et al. | |
| 2010/0029794 A1 | 2/2010 | Yilmaz et al. | 521/63 |
| 2010/0055667 A1 | 3/2010 | Hage et al. | |
| 2010/0075404 A1* | 3/2010 | Templeton | C12N 15/1003 435/280 |
| 2010/0099579 A1 | 4/2010 | Chilkoti et al. | 506/16 |
| 2010/0116743 A1 | 5/2010 | Pryor et al. | |
| 2010/0129830 A1 | 5/2010 | Deshayes et al. | 435/7.1 |
| 2010/0132251 A1 | 6/2010 | Sohling et al. | 44/388 |
| 2010/0156135 A1 | 6/2010 | Farokhzad et al. | 424/9.1 |
| 2010/0159254 A1 | 6/2010 | Oertli et al. | 428/447 |
| 2010/0181254 A1 | 7/2010 | Graalfs | 210/656 |
| 2010/0237019 A1 | 9/2010 | Aldegonda et al. | 210/670 |
| 2010/0255310 A1 | 10/2010 | Chen | 428/403 |
| 2010/0272996 A1 | 10/2010 | Homes et al. | 428/402 |
| 2010/0310539 A1 | 12/2010 | Garcia-Bennett | |
| 2010/0310865 A1 | 12/2010 | Kumar et al. | 428/352 |
| 2011/0017670 A1 | 1/2011 | Anderson | |
| 2011/0049042 A1 | 3/2011 | DiLeo et al. | 210/480 |
| 2011/0049056 A1 | 3/2011 | Wyndham et al. | 210/656 |
| 2011/0059845 A1* | 3/2011 | Fryxell | B01D 53/02 502/402 |
| 2011/0065901 A1 | 3/2011 | Soice et al. | 530/388.1 |
| 2011/0100915 A1 | 5/2011 | Kanda et al. | 210/656 |
| 2011/0121229 A1 | 5/2011 | Linder et al. | 252/184 |
| 2011/0139717 A1 | 6/2011 | Malenfant et al. | 210/656 |
| 2011/0160104 A1 | 6/2011 | Wu et al. | 507/269 |
| 2011/0162153 A1 | 7/2011 | Niembro et al. | 8/142 |
| 2011/0184154 A1 | 7/2011 | Zarbis-Papastoitsis et al. | |
| 2011/0186519 A1 | 8/2011 | Balayan et al. | 210/660 |
| 2011/0201078 A1 | 8/2011 | Rasmussen et al. | |
| 2011/0245077 A1 | 10/2011 | Anderson et al. | 502/402 |
| 2011/0284465 A1 | 11/2011 | Liu et al. | 210/656 |
| 2011/0313147 A1 | 12/2011 | Boschetti et al. | 536/56 |
| 2011/0313712 A1 | 12/2011 | Nikolyn et al. | 702/136 |
| 2012/0024791 A1 | 2/2012 | Deetz et al. | |
| 2012/0055860 A1 | 3/2012 | Wyndham | 210/198.3 |
| 2012/0065393 A1 | 3/2012 | Choi et al. | 540/456 |
| 2012/0071643 A1 | 3/2012 | Helfer et al. | 536/25.4 |
| 2012/0108803 A1 | 5/2012 | Han et al. | 536/24.5 |
| 2012/0205315 A1 | 8/2012 | Liu et al. | 210/656 |
| 2012/0231537 A1* | 9/2012 | Templeton | C12N 15/1003 435/320.1 |
| 2012/0259094 A1 | 10/2012 | Hearn et al. | 530/387.7 |
| 2012/0283337 A1 | 11/2012 | Brick et al. | 514/772.4 |
| 2013/0020523 A1 | 1/2013 | Han et al. | |
| 2013/0041135 A1 | 2/2013 | Tamori et al. | 530/387.1 |
| 2013/0046056 A1 | 2/2013 | Spector et al. | 525/54.1 |
| 2013/0056415 A1 | 3/2013 | Kozlov et al. | 210/636 |
| 2013/0109072 A1 | 5/2013 | Tsunoda et al. | |
| 2013/0112623 A1 | 5/2013 | Fernandez-Lahore et al. | |
| 2013/0122215 A1 | 5/2013 | Waller et al. | |
| 2013/0131321 A1 | 5/2013 | Bittermann et al. | |
| 2013/0133516 A1 | 5/2013 | Okano et al. | 95/88 |
| 2013/0146542 A1 | 6/2013 | Huang et al. | 210/656 |
| 2013/0178608 A1 | 7/2013 | Kulkarni et al. | |
| 2013/0189322 A1 | 7/2013 | Honeyman et al. | |
| 2013/0193052 A1 | 8/2013 | Witt et al. | |
| 2013/0245139 A1 | 9/2013 | Kozlov et al. | |
| 2013/0274451 A1 | 10/2013 | Bjorkman et al. | |
| 2013/0313187 A1 | 11/2013 | Yin et al. | 210/500.33 |
| 2014/0046023 A1 | 2/2014 | Gottschall et al. | B01J 20/286 |
| 2014/0046029 A1 | 2/2014 | Shannon et al. | C08F 271/02 |
| 2014/0093888 A1* | 4/2014 | Templeton | C12N 15/101 435/7.4 |
| 2014/0367338 A1 | 12/2014 | Gu et al. | |

FOREIGN PATENT DOCUMENTS

| | | |
|---|---|---|
| CN | 101381437 | 5/2011 |
| CN | 102443120 | 3/2013 |
| CN | 102675564 | 4/2014 |
| DE | 102006012467 A1 | 9/2007 |
| EP | 0172579 A2 | 2/1986 |
| EP | 0106769 B1 | 1/1987 |
| EP | 0263934 A1 | 4/1988 |
| EP | 0239079 | 7/1988 |
| EP | 0403700 | 8/1992 |
| EP | 0545677 A1 | 6/1993 |
| EP | 0300273 B1 | 3/1994 |
| EP | 0463036 B1 | 2/1995 |
| EP | 0520109 B1 | 3/1995 |
| EP | 0490300 B1 | 3/1998 |
| EP | 0950067 B1 | 10/1999 |
| EP | 1229094 B1 | 8/2002 |
| EP | 1758671 B9 | 3/2007 |
| EP | 1864999 B1 | 12/2007 |
| EP | 1897890 B1 | 3/2008 |
| EP | 1900751 B1 | 3/2008 |
| EP | 2217646 B1 | 8/2010 |
| EP | 2352771 B1 | 8/2011 |
| EP | 2616169 A2 | 7/2013 |
| JP | S5226386 A | 2/1977 |
| JP | 59050052 A | 3/1984 |
| JP | 59050054 A | 3/1984 |
| JP | S6486868 A | 3/1989 |
| JP | H02142798 A | 5/1990 |
| JP | 06016738 A | 1/1994 |
| JP | 8134138 A | 5/1996 |
| JP | 2001521507 A | 11/2001 |
| JP | 2003526796 A | 9/2003 |
| JP | 2008012460 A | 1/2008 |
| JP | 2009126948 A | 6/2009 |
| JP | 2011001336 A | 1/2011 |
| JP | 2011523624 A | 8/2011 |
| JP | 2012012334 A | 1/2012 |
| JP | 2012042477 A | 3/2012 |
| JP | 2012086221 A | 5/2012 |
| JP | 2012139678 A | 7/2012 |
| JP | 2013510918 A | 3/2013 |
| WO | 8303776 A1 | 11/1983 |
| WO | 1992002638 | 2/1992 |
| WO | 9400237 A1 | 1/1994 |
| WO | 9403268 A1 | 2/1994 |
| WO | 1994012526 | 6/1994 |
| WO | 9525789 A1 | 9/1995 |
| WO | 1996034883 | 11/1996 |
| WO | 9705174 A1 | 2/1997 |
| WO | 9831461 A1 | 7/1998 |
| WO | 1998058072 | 12/1998 |
| WO | 0102452 A1 | 1/2001 |
| WO | 0188520 A2 | 11/2001 |
| WO | 0228912 A2 | 4/2002 |
| WO | 2002074791 | 9/2002 |

(56) References Cited

FOREIGN PATENT DOCUMENTS

| | | |
|---|---|---|
| WO | 03031580 A2 | 4/2003 |
| WO | 03049671 A2 | 6/2003 |
| WO | 2003102184 | 12/2003 |
| WO | 2004009677 A1 | 1/2004 |
| WO | 2004015120 | 2/2004 |
| WO | 2004024318 A1 | 3/2004 |
| WO | 2004076511 A2 | 9/2004 |
| WO | 2006110314 A2 | 10/2006 |
| WO | 2008027262 A1 | 3/2008 |
| WO | 2008140652 A2 | 11/2008 |
| WO | 2008147717 A1 | 12/2008 |
| WO | 2009053317 A1 | 4/2009 |
| WO | 2009079325 A1 | 6/2009 |
| WO | 2009102207 A1 | 8/2009 |
| WO | 2009150402 A2 | 12/2009 |
| WO | 2010027955 A2 | 3/2010 |
| WO | 2010043700 | 4/2010 |
| WO | 2010043701 | 4/2010 |
| WO | 2010043703 | 4/2010 |
| WO | 2011012302 A1 | 2/2011 |
| WO | 2011025867 A1 | 3/2011 |
| WO | 2011107299 | 9/2011 |
| WO | 2012087231 A1 | 6/2012 |
| WO | 2013004587 A1 | 1/2013 |
| WO | 2013007793 A1 | 1/2013 |
| WO | 2013062105 A1 | 5/2013 |
| WO | 2013089477 A1 | 6/2013 |
| WO | 2014058570 A1 | 4/2014 |
| WO | 2014090838 | 6/2014 |
| WO | 2014094957 | 6/2014 |

OTHER PUBLICATIONS

Flashner, Michael; Ramsden, Hugh; Crane, Laura, "Separation of Proteins by High-Performance Anion-Exchange Chromatography", Analytical Biochemistry, n 135, p. 340-344 (1983).

Gu, Feng; Chodavarapu, Kiran; McCreary, Dennis; Plitt, Thomas; Tamoria, Edward; Ni, Michelle; Burnham, Jennifer; Peters, Michael; Lenhoff, Abraham, "Silica-Based Strong Anion Exchange Media for Protein Purification", Journal of Chromatography A, n 1376, p. 53-63 (2015).

Kang, Xuezhen; Bates, Ronald; Frey, Douglas, "High-Performance Chromatofocusing Using Linear and Concave pH Gradients Formed with Simple Buffer Mixtures II. Separation of Proteins", Journal of Chromatography A, n 890, p. 37-43 (2000).

Minow, Benjamin; Egner, Florian; Jonas, Franziska; Lagrange, Bertille, "High-Cell Density Clarification by Single-Use Diatomaceous Earth Filtration", BioProcess International, n 12, v 4, supplement (2014).

Schirmer, Emily; Kuczewski, Michael; Golden, Kathryn; Lain, Blanca; Bragg, Carissa; Chon, John; Cacciuttolo, Marco; Zarbis-Papastoitsis, Gregory, "Primary Clarification of Very High-Density Cell Culture Harvests by Enhanced Cell Settling", BioProcess International, p. 32-39 (2010).

PCT Search Report and Written Opinion for PCT/US2016/035683; dated Sep. 2, 2016.

Bach, Long Giang; Islam, Md. Rafiqul; Jeong, Yean Tae; Hwang, Ha Sao; Lim, Kwon Taek, "A Facile Synthesis of PMMA-Si02 Nanocomposites via Surface Initiated Radical Polymerization", Molecular Crystals and Liquid Crystals, 565(1), 78-87 (2012).

Banerjee, Jaya; Kumar, Rajesh; Srivastava, Abhishek; Behari, Kunj, "Graft Copolymerization of 2-Acrylamido-2-Methyl-1-Propanesulfonic Acid onto Carboxymethylcellulose (Sodium Salt) Using Bromate/Thiourea Redox Pair", Journal of Applied Polymer Science, 100(1), 26-34 (2006).

Binghe Gu, Yun Li and Lee, Milton L., "Polymer Monoliths with Low Hydrophobicity for Strong Cation-Exchange Capillary Liquid Chromatography of Peptides and Proteins", Analytical Chemistry, v 79, n 15, p. 5848-5855 (2007).

Bowes, Brian D., "Protein Transport and Adsorption in Polymer-Modified Ion-Exchange Media", University of Delaware, ProQuest Dissertations Publishing (2011).

Boyle, M.D.P., Reis, K.J. "Bacterial Fc Receptors", Nature Biotechnology 5, p. 697-703 (1987).

Breadmore, Michael C.; Shrinivasan, Sushil; Karlinsey, James; Ferrance, Jerome P.; Norris, Pamela M.; Landers, James P. "Towards a Microchip-Based Chromatographic Platform. Part 2: Sol-Gel Phases Modified with Polyelectrolyte Multilayers for Capillary Electrochromatography", Electrophoresis, v 24, p. 1261-1270 (2003).

Brunauer, Stephen, Emmett, P.H., Teller, Edward "Adsorption of Gases in Multimolecular Layers" Journal of American Chemical Soceity, 60, p. 309-319 (1938).

Bruno, G.; Gasparrini, F.; Misiti, D.; Arrigoni-Martelll. E.; Bronzetti, M. "High-performance liquid chromatographic separation of biomolecules using calcium phosphate supported on macroporous silica microparticles", Journal of Chromatography, v 504, n 2, p. 319-333, 19g0; ISSN: 00219673, Publisher: Elsevier.

Buess-Herman, Claudine et al. "Hydration of a Polysulfone Anion-Exchange Membrane Studied by Vibrational Spectroscopy," Langmuir, vol. 19, No. 8 (2003).

Capito, Florian; Bauer, Johann: Rapp, Almut; Schroter, Christian; Kalmar, Harald; Stanislawski, Bernd, "Feasibility Study of Semi-Selective Protein Precipitation with Salt-Tolerant Copolymers for Industrial Purification of Therapeutic Antibodies", Biotechnology and Bioengineering, v 110, n 11, p. 2915-2927 (2013).

Carrot, Geraldine; Perez, Henri, "Controlled Surface Initiated Polymerizations from Inorganic Nanoparticles", Polymer Preprints (American Chemical Society, Division of Polymer Chemistry), 47(2), 827-828 (2006).

Chen, Xin; Tolley, H. Dennis; Lee, Milton L., "Polymeric Cation-Exchange Monolithic Columns Containing Phosphoric Acid Functional Groups for Capillary Liquid Chromatography of Peptides and Proteins", Journal of Chromatography A, v 1217, n 24, p. 3844-3854 (2010).

Dhar, P.; Vatansever. F.; Seery, "Modification of Silica Surfaces Using Surface Initiated Polymerization", Book of Abstracts, 215th ACS National Meeting, Dallas, Mar. 29-Apr. 2, PMSE-147 (1998).

Dyer, Daniel J.; Zhao, Tongfeng; Green, John-Bruce, "Surface Initiated Photopolymerization from Gold", Polymer Preprints (American Chemical Society, Division of Polymer Chemistry), 42(2) (2001).

Emara, Samy; Masujima, Tsutomu; Hadad, Ghada: Kamal, Maha; Zaazaa, Hala; Kawi, Mohamed Abdel, "A Rapid, Sensitive, and Environmentally Friendly On-Line Solid Phase Extraction Using Protein-Coated IJ-Bondapak Cyanide Silica Precolumn for Chromatographic Determination of Paracetamol in Human Serum.", Journal of Liquid Chromatography and Related Technologies, v 36, n 10, p. 1297-1311, Apr. 1, 2013; ISSN: 10826076, E-ISSN: 1520572X; DOI: 10, 1080/10826076.2012,686139; Publisher: Taylor and Francis Inc.

Guo, Hui, "Development of Chromatofocusing Techniques Employing Mixed-Mode Column Packings for Biomolecule Separations", Dissertations & Theses, University of Maryland, Baltimore County, ProQuest, UMI Dissertations Publishing (2014).

Hatch, R.G., "Chromatography of Proteins on a Silica-Based Support with Polyethylene No Glycol ligands", Journal of Chromatographic Science, v 28, n 4, p. 210-214, Apr. 1990; ISSN: 00219665.

Hernstrom, Petrus et al. "Atom-Transfer Radical Graft Polymerization Initiated Directly from Silica Applied to Functionalization of Stationary Phases for High-Performance Liquid Chromatography in the Hydrophilic Interaction Chromatography Mode," Analytical Chemistry, 78 (2006), pp. 7098-7103.

Huang, Meiyu; Wu, Ru, "Polymerization of Acrylic Acid Initiated by Poly(y-mercaptopropylsiloxane-lanthanide) Complexes", Ziran Zazhi, 5(12), 950-1 (1982).

Jandera, Pavel, "Stationary phases for hydrophilic interaction chromatography, their characterization and implementation into multidimensional chromatography concepts." Journal of Separation Science, v 31, n 9, pp. 1421-1437, May 2008, Hydrophilic interaction chromatography; ISSN: 16159306, E-ISSN: 16159314; DOI: 10.1002/jssc.200800051, Publisher: Wiley-VCH Verlag.

(56) References Cited

OTHER PUBLICATIONS

Katoh, Shigeo et al. "Affinity Purification of Antibodies: Optimization Strategies of Protein A-Coupled Silica Media", G.I.T. Laboratory Journal May-Jun. 2007 p. 26-27.
Katoh, Shigeo, "Affinity chromatography for large-scale purification of antibody pharmaceuticals", Biotechnology-based drug manufacturing technology series. Pharm Tech Japan, v 27, No. 11, 2011.
Katoh, Shigeo; Imada, Masami; Takeda, Naoki; Katsuda, Tomohlsa; Miyahara, Hiroyoshi; Inoue, Masaki; Nakamura, Shuji, "Optimization of silica-based media for antibody purification by protein A affinity chromatography", Journal of Chromatography A, v 1161, n 1-2, p. 36-40, Aug. 17, 2007, 26th International Symposium on the Separation of Proteins, Peptides and Polynucleotfdes; ISSN: 00219673; DOI: 10.1016/j.chroma.2007,04.023; Publisher: Elsevier.
Kuroda, Hirofumi; Nakatsuchi, Sayaka; Kitao, Nobuyoshi; Nakagawa, Tsuyoshi; "Radical polymerization of Methacrylates Having Moiety Activated by Electron-Withdrawing Group as a Reactive Functional Group" Relative & Functional Polymers, v 66, p. 229-238 (2006).
Liu, Shu-juan; Dun, Hui-juan; Zhou, Feng; Zhao, Liang; Liu, Xia; Jiang, Sheng-xiang, "Preparation of Polymer Modified Stationary Phases through Surface Radical Chain Transfer Reaction" Sepu, 20(5), 432-435 (2002).
Liu, Shu-juan; Zhou, Feng; Jiang, Sheng-xiang; Liu, Wei-min, "Characterization of Polymer Brushes on Nanoparticle Surfaces" Gaofenzi Cailiao Kexue Yu Gongcheng, 19(6), 65-68 (2003).
Liu, Shu-juan; Zhou, Feng; Jiang, Sheng-xiang; Liu, Wei-min, "Preparation of Stationary Phase for HPLC Through Surface-Initiated Polymerization" Gaofenzi Cailiao Kexue Yu Gongcheng, 19(6), 65-68 (2003).
Ma, Z et al. "Synthesis of Magnetic Chelator for High-Capacity Immobilized Metal Affinity Adsorption of Protein by Cerium Initiated Graft Polymerization." Langmuir, vol. 21, No. 15 (2005).
Maiti, Sukumar; Palit, Santi "Thiols as Redox Initiator for Vinyl Polymerization" Journal of Polymer Science: Polymer Chemistry, v 9, n 1, p. 253-256 (1971).
Manda, Keerthini "Synthesis and characterization of protein bonded stationary phases for HPAC.", Source: Dissertations & Theses, 2007. vol. 46, Issue 1, Publication I order No. AAI1445247; http://search.proquest.com/docviewf33934537?accountid=142944.
Massom, L R; Ulbright, C; Snodgrass, P; Jarrett, H W, "Protein A-silica: Purification of Antibodies and Antigen/Antibody Complexes by High Pressure Affinity Chromatography", Biochromatography 4.3 (1989): 144-148; http://search.proquest.com/docview/15419101?accountid=142944.
McCue, Justin T.; Kemp, Glen; Low, Duncan; Quiniones-Garcia, Igor, "Evaluation of protein-A chromatography media", Science Direct_Journal of Chromatography A, 989 (2003) 139-153.
Mihai, M.; Schwarz, S.; Janke, A; Ghiorghia, C.A.; Dragan, E.S., "Silica Microparticles Surface Coating by Layer-by-Layer or Polyelectrolyte Complex Adsorption", Periodical: Journal of Polymer Research, v 20, n 2, 89 (2013).
Min, Jun Ho; Min, Seong Kee, "The Characteristics of Poly(acrylamide)-SiOx Nanoparticles Prepared by Graft-Polymerization", Periodical: Kongop Hwahak, 21(1), 34-39 (2010).
Miyahara, H; Nakashima, R; Inoue, M; Katsuda, T; Yamaji, H. Katoh, S; "Optimization and Performance of Silica-Based Media for Industrial-Scale Antibody Purification" Chemical Engineering & Technology (2012), 35, No. 1, 157-160. Publisher. Wiley-VCH Verlag.
Moon, Jung-Min et al. "Modification of Monodisperse Colloidal Silica by Radical Copolymerization of Cationic Surface Active Vinyl Monomers," Polymer Journal, vol. 41, No. 3 (2009), pp. 208-213.
Mori, Hideharu et al. "Controlled Radical Polymerization of an Acrylamide Containing I-Phenylalanine Moiety via RAFT." Macromolecules, No. 38, p. 9055-9065 (2005).
Murofushi, Katsumi, "Additive for Increase in Hardness and Adhesiveness of Photocurable Resin", Periodical: Purasuchikkusu, 57(9), 37-40 (2006).

Narayanan, S.; CraneS., "Affinity Chromatography Supports: A Look at Performance Requirements", Trends in Biotechnology, vol. 8, 1990, pp. 12-16; DOI: 10.1016/0167-7799(90)90124-G; Publisher: Elsevier.
Ohlson S, Wieslander J, "High-Performance Liquid Affinity Chromatographic Separation of Mouse Monoclonal Antibodies with Protein a Silica.", J Chromatogr. Jun. 26, 1987;397:207-12; Publisher: Elsevier.
Okaya, Takuji; Kikuchi, Kanji; Morii, Yukiko "Polymerization of Acrylamide in Aqueous Medium Initiated with a Redox System Composed of Cysteine and Potassium Bromate" Macromolecular Chemistry and Physics, v 198, p. 2027-2034 (1997).
Park, Mi•kyoung; Sakellariou, George; Pispas, Stergios; Hadjichristides, Nikos; Mays, Jimmy; Advincula, Rigoberto, "Living Anionic Surface Initiated Polymerization (LASIP): Synthesis and Characterization of Block Copolymers", Periodical: Abstracts of Papers, 223rd ACS National Meeting, Orlando, FL, United States, Apr. 7-11, 2002.
Prucker, Oswald; Habicht, Jorg; Park, In-Jun; Ruhe, Jurgen, "Photochemical Strategies for the Preparation, Micropatterning and Modification of Polymer Brushes", Periodical: Polymer Preprints (American Chemical Society, Division of Polymer Chemistry), 44(1), 470-471 (2003).
Rashid, Harun-Or; Lee, Won-Ki; Hong, Seong-Soo; Park, Jong Myung; Kim, Hyun Gyu; Um, Kwon Taek "Polymer Brushes on Carbon Nanotubes by Thioi-Lactam Initiated Radical Polymerization of 2-Hydroxyethyl Methacrylate", Journal of Nanoscience and Nanotechnology, v 12, p. 840-846 (2012).
Roy, Asit; Roy, Sujata, "Preparation of a high flow packing material (silica based) for high performance affinity chromatography of proteins." Affinity Chromatography and Biological Recognition, 1983, AMF Speciality Materials Group Meriden, Connecticut, USA, ISBN 0-12-166580-1. Publisher: Academic Press, Inc.
Salarizadeh, Parisa; Javanbakht. Mehran; Abdollahi, Mandi; Naji, Leila, "Preparation, Characterization and Properties of Proton Exchange Nanocomposite Membranes Based on Poly(Vinyl Alcohol) and Poly(Sulfonic Acid)-Grafted Silica Nanoparticles" International Journal of Hydrogen Energy, v 38, n 13 (2013).
Savina, Irina et al. "Anion-Exchange Supermacroporous Monolithic Matrices with Grafted Polymer Brushes of N,N-Dirnethylaminoethyi-Methacrylate," Journal of Chromatography A, vol. 1092, No. 2 (2005).
Savina, Irina et al. "ion-Exchange Macroporous Hydrophilic Gel Monolith with Grafted Polymer Brushes." J. Mol. Recognit., vol. 19, No. 4 (2006).
Schmidt, D.E.; Giese, R.W.; Conran, D.; Karger, B.L, "High performance liquid chromatography of proteins on a dial-bonded silica gel stationary phase", Analytical Chemistry, v 52, n 1, 177-82, Jan. 1980; ISSN: 0003-2700; Country of publication: USA. Publisher. American Chemical Society.
Shimomura, Masato; Kikuchi, Hiroaki; Matsumoto, Hiroshi; Yamauchi, Takeshi; Miyauchi, Shinnosuke "Attaching of Poly(acrylic acid) to Inorganic Surface and its Application to Enzyme Immobilization" Polymer Journal, v 27, n 9, p. 974-977 (1995).
Shukla, J.S.; Singh, Khajan "Aqueous Polymerization of Acrylamide", Journal of Polymer Science: Polymer Chemistry Edition, vol. 17, 531-538 (1979).
Srivastava, Arti; Behari, Kunj, "Graft Copolymerization of 2-Acrylamido-2-Methyi-1-Propane Sulphonic Acid onto Xanthan Gum by Ascorbic / Bromate Redox Pair" PMSE Preprints, 90, 698-699 (2004).
Tessrkmen, Deniz et al. "Synthesis of Tentacle-Type Magnetic Beads as Immobilized Metal-Chelate Affinity Support for Cytochrome C Adsorption," Int. J. Bioi. Macromol., vol. 38, No. 2 (2006).
Tsuneda, Setal. "Biding of Lysozyme onto a Cation-Exchange Microporous Membrane Containing Tentacle-Type Grafted Polymer Branches," Biotechnol Prog., vol. 10, No. 1 (1994).
Vuignier, Kanne; Fekete, Szabolcs; Carrupt, Pierre-Aiain; Veuthey, Jean-Luc; Guillarme, Davy, "Comparison of Various Silica-Based Monoliths for the Analysis of Large Biomolecules", Journal of Separation Science, v 36, n 14, p. 2231-2243, Jul. 2013; ISSN: 16159306, E-ISSN: 16159314; DOI: 10.1002/jssc.201300323; Publisher: Wiley.VCH Verlag.

(56) References Cited

OTHER PUBLICATIONS

Wang, Xiao-hua; Gao, Bao-jlao; Wang, Ming-juan; Fang, Xiao-lin, "Realizing Highly Effective Graft-Polymerization of Acrylonitrile on Surfaces of Silica Gel Particles by Constructing Mercapto Group-Cerium (IV) Salt Redox Initiation System" Gaofenzi Xuebao, (3), 256-263 (2012).

Wei, Bingchuan, "Silica colloidal crystals for ultra-efficient protein separations", Dissertations & Theses, Purdue University, ProQuest, UMI Dissertations Publishing, 2011. 3506193; ISBN 9781267315243; http://search.proquest.com/docview/1014174524?accountid=142944, Publisher. UMI Dissertations Publishing 2011.

Xu, Liang et al. "Fabrication and Characterization of Open-Tubular CEC Modified with Tentacle-Type Metal Chelating Polymer Chains," Electrophoresis, vol. 28, No. 11 (2007).

Xu, Liang et al. "Novel Negatively Charged Tentacle-Type Polymer Coating for On-Line Preconcentration of Proteins in CE." Electrophoresis, vol. 30, No. 4 (2009).

Xu, Liang et al. "Novel Open Tubular CEC with Tentacle-Type Polymer Stationary Phase Functionalized by Phenylalanine." Electrophoresis, vol. 29, No. 4 (2008).

Yanase, Tomohiro et al. "Regeneration Technology of Tetramethylammonium Hydroxide Using ton Exchange Resin." Technology Reports of Kansai University, No. 47 (2005).

Yoshinaga, Kohji; Kondo, Akihiko; Higashitani, Ko; Kito, Taketoshi, "Immobilization of Protein on Monodispersed Colloidal Silica with Poly(Ethylene Glycol) Spacer and Application of the Composites to Immunological Agglutination Tests", Colloids and Surfaces A: Physicochemical and Engineering Aspects, v 77, n 2, p. 101-107, Sep. 17, 1993; ISSN: 09277757; DOI: 10.1 016/0927-7757(93)80106-0.

Zhang, Jian et al. "Capillary Electrochromatography of Peptides on a Column Packed with Tentacular Weak Cation-Exchanger Particles," Journal of Chromatography A, 953 (2002), pp. 239-249.

Zhang, Wenjun; Hu, Baoan; Zhang, Yan; Su, Hui; Xiao, Min, "Preparation of Novel Amphiphilic Polymeric Flocculant by Dispersion Polymerization Method", Huaxue Gongcheng, 37(2), 67-70 (2009).

* cited by examiner

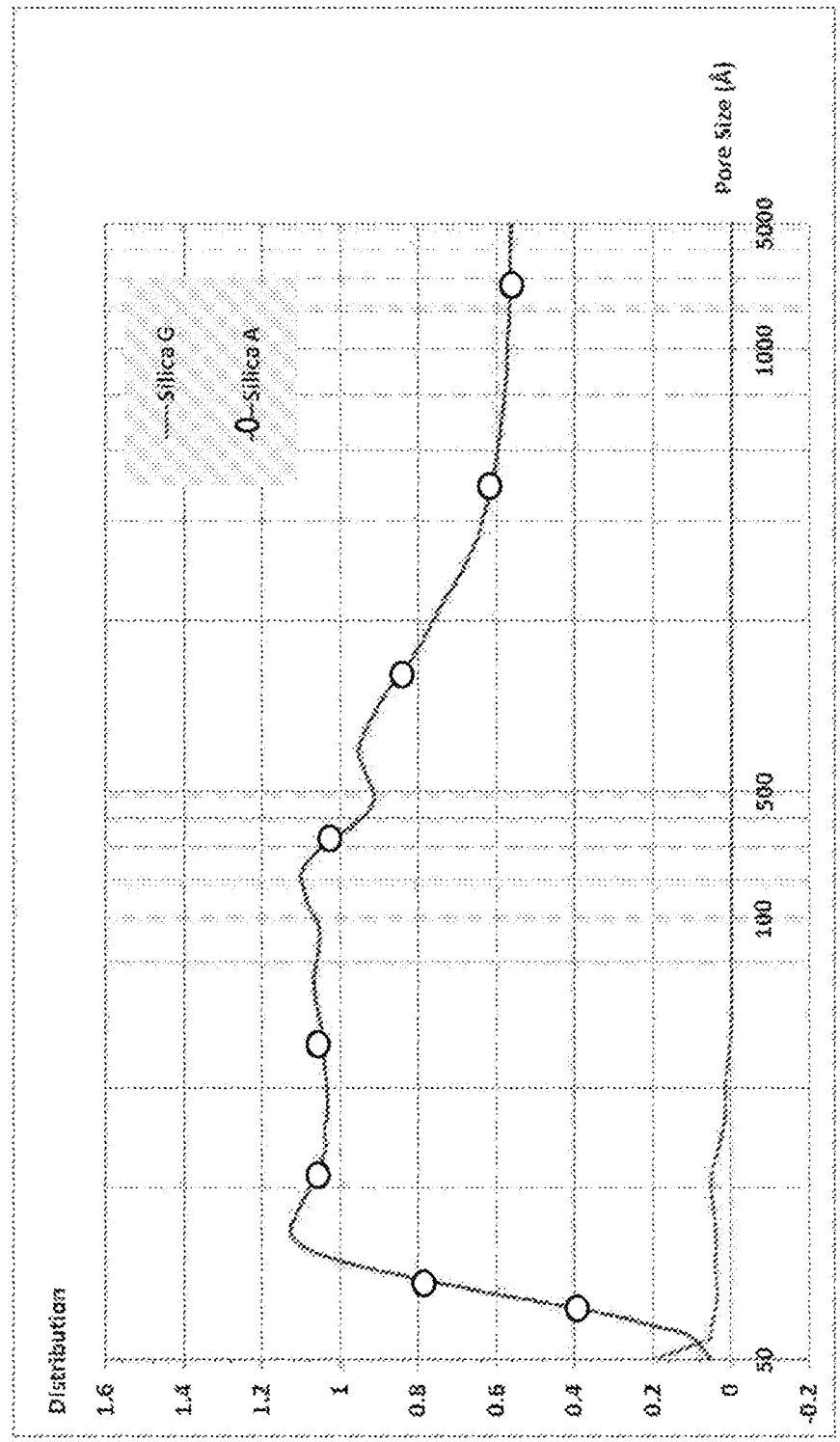

ADSORBENT BIPROCESSING CLARIFICATION AGENTS AND METHODS OF MAKING AND USING THE SAME

FIELD OF THE INVENTION

The present invention is directed to adsorbent clarification agents suitable for use in bioprocessing procedures. The present invention is further directed to methods of making and using adsorbent clarification agents for the removal of or separation of undesirable biological substances during bioprocessing procedures.

BACKGROUND

In recent years biopharmaceutical manufacturing has demonstrated major improvements in MAb production, exhibiting product titers as high as 25 g/L often associated with very high cell densities. High-density cell cultures with >150 million cells/mL pose a great challenge in further downstream processing because of a need to remove a large amount of biomass and increased levels of contaminants from cell debris generated during cell culture and harvesting. Production of biological substances (MAbs, in particular) usually involves processing a complex cell culture broth from which desired biological substances must be isolated and purified while maintaining high overall product recovery and quality. Traditionally, centrifugation and a combination of filtration techniques (tangential-flow filtration and depth filtration) have been widely accepted as workhorses for clarifying these complex cell culture broths. However, improvement of mammalian cell culture processes is providing for total cell densities far beyond traditional levels of $20 \times 10^6$ cells/mL for CHO cells to $>150 \times 10^6$ cells/mL for PER.C6 cells. Thus, limitations of both centrifugation and filtration techniques are apparent by the high ($\leq 40\%$) solids content of such harvests.

Centrifugation can be applied to process feed streams with high levels of solids, for instance. However, product recovery can be low because of increased pellet volumes and a need to desludge frequently (especially in large-scale continuous centrifugation). Additionally, cell disruption from shear forces generated during centrifugation can further decrease the efficiency of harvest clarification and potentially cause product damage and/or entrapment.

Depth filters are advantageous because they remove contaminants, and many come in single-use format, reducing the need for cleaning and validation. However, depth filters are currently unable to handle high-solids feedstreams and are often used in series with centrifugation. TFF can handle high solids loading, but this technique can exhibit poor yield because of polarization of solids at the membrane surface when processing highly dense feed streams. Excessive product dilution and cell lysis caused by shear forces can also limit the utility of TFF.

Flocculation of cell culture harvests has also been widely used to enhance clarification throughput and downstream filtration operations. Current techniques include the use of soluble polyionic polymers (such as DEAE dextran, acryl-based polymers, and polyethylene amine) and inorganic materials such as diatomaceous earth and perlites, which remove cells and cell debris. However, polymers must subsequently be removed from process streams, which requires monitoring and quantification by in-process and product-release assays. If IEX chromatography is included as a purification step in the downstream process, binding capacities will be greatly affected by the charged nature of flocculants. The high viscosity of polycation stock solutions presents an additional process challenge.

In recent years, various new clarification techniques have been developed. For example, (http://www.selectscience.net/product-news/sartorius-stedim-biotech) single use harvesting technology for high cell density cultures using diatomaceous earth (DE) as filter aid has been introduced. (Minow B., et al, BioProcess Int., Apr. 1, 2014). However, given its low surface area (BET~1 $m^2/g$) and non-porous nature, DE has no function in adsorption of proteins and/or other types of biologics, but only as filter aid.

In other processes, functionalized particulate materials have been used as adsorbents for clarification of cell broths. For example, WO2010043700 and WO2010043703 methods of clarification or removing host cell proteins by the utilization of anion exchange material in the process. The property or optimal conditions for the ion exchange materials are not described in the patent applications.

Efforts continue to further develop clarification materials and processes having improved agents in the form of functionalized particulate materials so as to improve binding capacity (i.e., the amount and the variety of biomaterials that can be bound to the adsorbent clarification agents) and/or binding selectivity of the functionalized particulate materials.

SUMMARY

The present invention addresses the need in the art for improved bioprocesses by the discovery that the use of certain functionalized porous inorganic oxide materials provide enhanced performance as clarification adsorbents. The adsorbents of the present invention unexpectedly provide exceptional binding capacity, as well as binding selectivity in bioprocesses (e.g., biopurification, bioseparation, etc.) when compared to known functionalized particulate materials.

In particular, the present invention provides improved bioprocesses employing polymeric functionalized inorganic oxide materials comprised of porous inorganic oxide particles having a sufficiently wide pore size distribution to enable the particles to capable of selectively bind to a wide variety of biomolecules including, but not limited to, cells, host cell proteins, nucleic acids, cell debris, chromatins, etc., so as to remove these materials during one or more processing steps. In some embodiments, the porous inorganic oxide particles have a pore size distribution as measured by a pore size distribution span 90 value of at least about 1.0. In other embodiments, wherein the porous particles having a pore size distribution as measured by a pore size distribution span 90 value of as much as about 5.0 to about 10.0.

Accordingly, the present invention is directed to polymer functionalized porous inorganic oxide particles having a specified pore size distribution (also referred to herein as "adsorbents") which are useful as clarification agents in a variety of bioprocesses. In one exemplary embodiment, the present invention is directed to adsorbents comprising polymeric material covalently bonded to the surface of porous inorganic oxide particles wherein said particles have a pore size distribution as measured by a pore size distribution span 90 value of at least about 1.0. In some desired embodiments, the invention comprise the adsorbents useful as a bioprocessing clarification agent, wherein the adsorbents comprise a polyelectrolyte material covalently bonded to the surface of porous inorganic oxide particles, wherein the porous particles having a pore size distribution as measured by a pore size distribution span 90 value of as much as about 5.0 to about 10.0. In preferred embodiments of the invention, the polymeric material comprises a polyelectrolyte, e.g. polyethyleneimine. In an even more preferred embodiment of the invention, the porous metal oxide particle comprise silica.

The present invention is even further directed to methods of making adsorbents in the form of functionalized particulate material. In one exemplary embodiment, the method of making adsorbents of the present invention comprises: contacting porous inorganic metal oxide particles with one or more reactants under reaction conditions that result in at least one polymeric material covalently bonded to at least one surface of the metal oxide particles, wherein the metal oxide particles have a wide pore size distribution as measured by a pore size distribution span 90 value of at least about 1.0.

The present invention is also directed to a method for the clarification of a bioprocess mixture during a bioprocessing procedure. The method provides for the removal or separation of the undesirable biological substances, e.g. cell debris, from a bioprocessing mixture by using the absorbents of the invention.

These and other features and advantages of the present invention will become apparent after a review of the following detailed description of the disclosed embodiments and the appended claims.

BRIEF DESCRIPTION OF THE DRAWINGS

FIGURE graphically shows the comparison in pore size distributions (from mercury porosimetry) for two different silicas.

DETAILED DESCRIPTION

To promote an understanding of the principles of the present invention, descriptions of specific embodiments of the invention follow and specific language is used to describe the specific embodiments. It will nevertheless be understood that no limitation of the scope of the invention is intended by the use of specific language. Alterations, further modifications, and such further applications of the principles of the present invention discussed are contemplated as would normally occur to one ordinarily skilled in the art to which the invention pertains.

It must be noted that as used herein and in the appended claims, the singular forms "a", "and", and "the" include plural referents unless the context clearly dictates otherwise. Thus, for example, reference to "an oxide" includes a plurality of such oxides and reference to "oxide" includes reference to one or more oxides and equivalents thereof known to those skilled in the art, and so forth.

"About" modifying, for example, the quantity of an ingredient in a composition, concentrations, volumes, process temperatures, process times, recoveries or yields, flow rates, and like values, and ranges thereof, employed in describing the embodiments of the disclosure, refers to variation in the numerical quantity that may occur, for example, through typical measuring and handling procedures; through inadvertent error in these procedures; through differences in the ingredients used to carry out the methods; and like proximate considerations. The term "about" also encompasses amounts that differ due to aging of a formulation with a particular initial concentration or mixture, and amounts that differ due to mixing or processing a formulation with a particular initial concentration or mixture. Whether modified by the term "about" the claims appended hereto include equivalents to these quantities.

As used herein, the terms "bioprocess" or bioprocessing" refer to a batch process that forms, alters and/or utilizes one or more biomolecules. The term "bioprocess" includes, but is not limited to, bioseparation processes, biopurification processes, processes for forming biopharmaceuticals, and processes for purifying biopharmaceuticals. As used herein, the term "bioprocess" or bioprocessing" refers to processing that may take place prior to a chromatography process (e.g., removing cell debris from a batch of material), does not encompass chromatography processes (e.g., liquid chromatography).

As used herein, the term "biomolecule" means any molecule that is produced by a living organism, including large molecules such as proteins, polysaccharides, lipids, and nucleic acids; and small molecules such a primary metabolites, secondary metabolites, and natural products. Examples of biomolecules include cells and cell debris; antibodies, proteins and peptides; nucleic acids, such as DNA and RNA; endotoxins; viruses; vaccines and the like. Other examples of biomolecules include those recited in WO 2002/074791 and U.S. Pat. No. 5,451,660.

As used herein, "porous inorganic metal oxide particles" includes particles comprised of inorganic metal oxide materials having intra-particle pores or inter-particle pores in cases where smaller particles are agglomerated to form larger particles Inorganic metal oxides include, but is not limited to, silica, alumina, zirconia or the combination of them.

As used herein, the term "functionalized" as it relates to the surface of the inorganic oxide particles means porous inorganic metal particles that have been surface modified by reaction with at least one functional compound to alter the selectivity of at least a portion of the particle surface, including the surface area on the external portion of the particles, and/or on the surface area of the internal pores. The functionalized surface of the particles may be used to form a bonded phase (covalently or ionically), a coated surface (e.g., reverse phase C18 bonded), a polymerized surface (e.g., ion exchange), an inherent surface (e.g., inorganic/organic hybrid material), or the like. For example, reacting porous inorganic oxide particles with octadecyltrichlorosilane forms a "reverse phase" by covalently bonding the silane to the inorganic surface (e.g., C4, C8, C18, etc.). In another example, reaction of the inorganic particles with aminopropyltrimethoxysilane followed by quaternization of the amino group forms an "anion exchange phase." In a third example, a bonded phase may be formed by reaction of the inorganic particles with aminopropyltrimethoxysilane followed by formation of an amide with an acid chloride. Other bonded phases include diol, cyano, cation, affinity, chiral, amino, C18, hydrophilic interaction (HILIC), hydrophobic interaction (HIC), mixed mode, size exclusion, etc. As part of the bonded phase or functionalized surface, a ligand may be used to show specific interaction with the target molecule or biomolecule (e.g., ligate), such as those set forth in U.S. Pat. No. 4,895,806.

As used herein, the term "polyelectrolyte" is defined as meaning a polymer comprising repeating units such as (i) a cation, (ii) an anion, or (iii) an electrolyte functional group that associates or dissociates with a proton in aqueous solutions to form a positive or negative charge. For example, cationic polyelectrolytes suitable for use in the present invention include, but are not limited to, polyethyleneimine (PEI), polyallylamine, polyvinyl pyridine, polydiallyldimethylammonium chloride (pDADMAC), and copolymers containing similar functional groups. Anionic polyelectrolytes suitable for use in the present invention include, but are not limited to, polyacrylic acids, polymethacrylic acids, polystyrene sulfonic acids, nucleic acids, and copolymers containing similar functional groups (e.g., poly(styrene-co-maleic acid, poly(styrene sulfonic acid-co-maleic acid))

As used herein, the term "polyethyleneimine" is defined as meaning a polymer comprising repeating units of an amine bonded to a —$CH_2CH_2$— spacer, wherein the polymer may be linear or branched and may contain primary, secondary and/or tertiary amino groups.

As used herein, the term "BET particle surface area" is defined as meaning a particle surface area as measured by the Brunauer Emmet Teller nitrogen adsorption method.

As used herein, the term median pore diameter (size) distributions were measured by mercury intrusion using an Autopore® IV 9520, available from Micromeritics Instrument Corporation (Norcross, Ga.).

As used herein, the term "pore size distribution" means the relative abundance of each pore size in a representative volume of porous inorganic particles.

As used herein "median pore diameter" is the Median pore diameter (PD50) is defined as the midpoint at which 50% of the pore volume is contributed by smaller pores and 50% is contributed by larger pores.

As used herein, the term "pore volumes" referenced herein represent cumulative volumes from mercury intrusion into 50-10,000 Å size pores.

As used herein, the term "molecular weight" is defined as meaning the molar mass of a single molecule of a particular compound or polymer.

As used herein, the "pore size distribution span 90 value" is calculated as [(PD90–PD10)/PD50], whereas PD10 is the pore diameter at 10% cumulative pore volume contribution, PD50 is the pore diameter at 50% cumulative pore volume contribution, and PD90 is the pore diameter at 90% cumulative pore volume contribution, all based on mercury intrusion data.

Porous Particles

As discussed above, the porous inorganic metal oxide particles useful to prepare the adsorbents of the present invention possess a wide pore size distribution as measured by a pore size distribution span 90 value of at least about 1.0 (or at least about 2.0, or at least about 3.0, or at least about 4.0, or at least about 5.0, or at least about 6.0, or at least about 7.5, desirably, from about 5.0 to about 10.0, more desirably, from about 7.5 to about 8.5, and in some embodiments, about 7.8). The wide pore size distribution enables the formation of adsorbent clarification agents that provide exceptional binding capacity, binding selectivity, as well as binding of a wide variety of biomolecules.

Generally, the porous inorganic metal oxide particles have a pore size distribution of from about 30 to about 5000 Å.

Advantageously, the wide pore size distribution of the porous inorganic metal oxide particles used to form the adsorbents of the present invention enables controlled binding capacity, binding selectivity, and binding of a wide variety of biomolecules by choosing (1) specific polymeric material bound to surfaces of the metal oxide particles, (2) the amount of polymeric material bound to surfaces of the metal oxide particles, and/or (3) the molecular weight of the polymeric material bound to surfaces of the metal oxide particles. As shown and discussed in the example section below, the wide pore size distribution of the metal oxide particles used to form the adsorbents of the present invention provides more flexibility and binding capacity when compared to known, commercially available adsorbents.

Typically, the porous metal oxide particles useful to prepare the adsorbents of the invention possess a median pore size of at least about 100 Å. In another embodiment, the porous inorganic particles have a median pore size of at least about 150 Å (or at least about 200 Å; or at least about 250, or at least about 300 Å; or at least about 350 Å; or at least about 400 Å, or at least about 500 Å; or at least about 600 Å; or at least about 800 Å. In some embodiments, the porous inorganic particles have a median pore size of from about 100 Å to about 800 Å. In some embodiments, the porous inorganic particles have a median pore size of from about 150 Å to about 250 Å. In other embodiments, the porous inorganic particles have a median pore size of less than 2000 Å. In other embodiments, the porous inorganic particles have a median pore size of less than 1000 Å.

The metal oxide particles typically have a particle size, as measured by a median particle dimension, of less than 150 μm. The porous inorganic metal oxide particles typically have a median particle dimension of about 1 μm, more typically, less than about 100 μm. In some embodiments, the porous inorganic particles have a median particle dimension of from about 10 to about 50 μm, more desirably, about 30 μm.

Typically, the metal oxide particles typically have an irregular shape, but may have any shape (e.g., spherical, elliptical, etc.). Regardless of shape, the porous inorganic metal oxide particles typically have a median particle dimension as discussed hereinabove.

In additional embodiments, the porous inorganic metal oxide particles may have an aspect ratio of at least about 1.0 as measured, for example, using Transmission Electron Microscopy (TEM) techniques. As used herein, the term "aspect ratio" is used to describe the ratio between (i) the median particle dimension of the porous inorganic particles and (ii) the median cross-sectional particle dimension of the porous inorganic particles, wherein the cross-sectional particle dimension is substantially perpendicular to the largest particle dimension of the porous inorganic particles. In some embodiments of the present invention, the porous inorganic particles have an aspect ratio of at least about 1.1 (or at least about 1.2, or at least about 1.3, or at least about 1.4). Typically, the porous inorganic particles have an aspect ratio of from about 1.0 to about 1.5.

The pore volume of the porous inorganic metal oxide particles as measured by mercury intrusion into 50-10,000 Å size pores is at least about 0.25 cc/g. In another embodiment, the pore volume of the porous inorganic metal oxide particles as measured by mercury intrusion into 50-10,000 Å size pores is at least 0.50 cc/g. In one exemplary embodiment of the present invention, the porous inorganic particles have a pore volume as measured by mercury intrusion into 50-10,000 Å size pores is at least about 1.0 cc/g; at least about 1.50 or at least about 1.77 cc/g. In another exemplary embodiment of the present invention, the porous inorganic particles have a pore volume as measured by mercury intrusion into 50-10,000 Å size pores of from about 1.0 cc/g to about 3.0 cc/g.

The surface area of porous inorganic metal oxide particles also have a surface area as measured by the BET nitrogen adsorption method (i.e., the Brunauer Emmet Teller method) of at least about 100 $m^2/g$, or at least about 300 $m^2/g$, or at least about 500 $m^2/g$. In one exemplary embodiment of the present invention, the porous inorganic oxide particles have a BET surface area of from about 100 $m^2/g$ to about 1000 $m^2/g$, or from about 600 $m^2/g$ to about 800 $m^2/g$. In a further exemplary embodiment of the present invention, the porous inorganic oxide particles have a BET surface area of from about 700 $m^2/g$.

The porous inorganic metal oxide particles useful to prepare the adsorbents of the invention may comprise a variety of inorganic materials including, but not limited to, silica, alumina, zirconia, or mixtures thereof. In one desired embodiment, the metal oxide particles comprise silica. When the metal oxide particles comprise silica, the particles desirably comprise silica having a purity of at least about 93% by weight $SiO_2$, or at least about 93% by weight $SiO_2$, at least about 94% by weight $SiO_2$, at least about 95% by weight $SiO_2$, at least about 96% by weight $SiO_2$, at least about 97% by weight $SiO_2$, or at least about 98% by weight $SiO_2$ up to 100% by weight $SiO_2$ based upon the total weight of the particle.

Adsorbents

In accordance with the present invention, the absorbent comprises porous metal oxide particles as described herein above and a polymeric material covalently bonded to surfaces of said metal oxide particles. In one embodiment the adsorbents comprises at least one bifunctional moiety extending from said surfaces of said metal oxide particles, each of said at least one bifunctional moiety comprising (i) one or more functional groups capable of bonding to said surfaces, and either (iia) said polymeric material, or (iib) one or more reactive groups capable of bonding to said polymeric material.

In another embodiment, the adsorbents comprises at least one bifunctional moiety extending from the surfaces of said metal oxide particles, each of said at least one bifunctional moiety comprising (i) one or more functional groups capable of bonding to said surfaces, and (iia) said polymeric material.

In yet another embodiment, the adsorbents comprises at least one bifunctional moiety extending from said surfaces of said metal oxide particles, each of said at least one bifunctional moiety comprising (i) one or more functional groups capable of bonding to said surfaces, and (iib) one or more reactive groups capable of bonding to said polymeric material.

Suitable bifunctional moiety extending from the surface of said metal oxide particle comprises epoxy rings that can react with amine groups from the polymer chains of the polyelectrolytes. In one embodiment, the at least one bifunctional moiety comprising the adsorbent comprises product from reaction of metal oxide surface with an epoxy silane. In a preferred embodiment, the epoxy siliane comprises (3-glycidoxypropyl)-trimethoxysilane.

In one embodiment of the invention, the polymeric material is covalently bonded to the surface of the metal oxide particles via a covalent bond linkage consisting of one or more atoms selected from the group consisting of C, O, Si and N.

Typically, the polymeric material comprises a polyelectrolyte. The polyelectrolyte may be cationic or anionic. Suitable cationic polyelectrolyte materials comprise polyethyleneimine, polyallylamine, polyvinyl pyridine, polydiallyldimethylammonium chloride (pDADMAC), a copolymer containing one or more cationic or cationic-forming functional groups, or combinations thereof. The cationic polyelectrolyte may also comprises a reaction product of said metal oxide particles and an aqueous trimethoxysilyl-polyethyleneimine solution. In a preferred embodiment, the polymeric material comprises polyethyleneimine. In even more preferred embodiment, the polyethyleneimine have (i) a weight average molecular weight, Mw, and (ii) a number average molecular weight, Mn, each of which is less than about 5000. In still a more preferred embodiment, the polyethyleneimine has (i) a weight average molecular weight, Mw, and (ii) a number average molecular weight, Mn, each of which ranges from about 500 to about 2500; or. (i) a weight average molecular weight, Mw, ranging from about 800 to about 2000, and (ii) a number average molecular weight, Mn, ranging from about 600 to about 1800.

In one embodiment, the polymeric material comprise a polyethyleneimine has a structure:

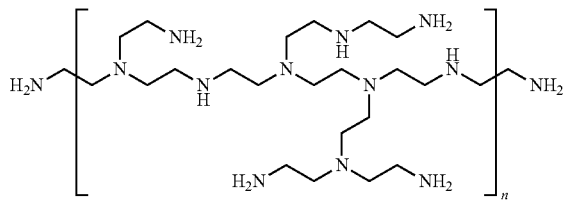

prior to being covalently bonded to said surfaces, and n is a number greater than or equal to 1.

Suitable anionic polyelectrolyte materials comprises polyacrylic acid, polymethacrylic acid, polystyrene sulfonic acid, nucleic acid, a copolymer containing one or more anionic or anionic-forming functional groups or combinations thereof. In a preferred embodiment, the anionic polyelectrolyte material comprises polyacrylic acid, polymethacrylic acid, or a combination thereof. In a more preferred embodiment, the anionic polyelectrolyte material comprise a polyacrylic acid or a polymethacrylic acid having a weight average molecular weight, Mw, greater than about 50,000. In an even more preferred embodiment, the polyacrylic acid or polymethacrylic acid has a weight average molecular weight, Mw, of from about 100,000 to about 250,000.

The amount of the polymeric material present in the absorbent is any amount suitable to provide charge interactions with biologics and therefore selectively bind to these biologics of opposite charge. In one embodiment, the polymeric materials comprise an amount such that less than 100% of said surfaces of the metal oxide particles are bonded to said polymeric material. In another embodiment, said the polymeric material is present on the adsorbent in an amount representing up to about 20.0 wt % of said adsorbents based on a total weight of said adsorbents. In other embodiments, the polymeric material is present in an amount representing from about 1.0 to about 15.0 wt % of said adsorbents based on a total weight of said adsorbents.

In a preferred embodiment of the invention, the porous metal oxide particles comprising the adsorbents comprise silica particles.

Methods of Making Adsorbents

The absorbent of the invention are generally prepare contacting the metal oxide particles with one or more reactants under reaction conditions that result in covalently bonding the polymeric material to the surfaces of the metal oxide particles. The contacting step may utilize a solvent. In one embodiment, the contacting step utilizes a reaction mixture free of organic solvent.

In one embodiment of the invention, the one or more reactants comprise at least one bifunctional compound comprising (i) one or more functional groups capable of bonding the compound to the surfaces of the metal oxide particles, and either (iia) the polymeric material, or (iib) one or more reactive groups capable of bonding to the polymeric material.

Suitable reactants comprising least one bifunctional compound comprising (i) one or more functional groups capable of bonding the compound to the surfaces of the metal oxide particles, and (iia) the polymeric material include, but is not limited to, polyethyleneimines.

Suitable reactants comprising at least one bifunctional compound comprising (i) one or more functional groups capable of bonding the compound to the surfaces of the metal oxide particles, and (iib) one or more reactive groups capable of bonding to the polymeric material, include but is not limited to, polyacrylic acids.

It is also within the scope of the invention to choose the one or more reactants so as to produce adsorbents having a desired degree of affinity for one or more particular biological compounds through attraction due to opposite charges. For example, the affinity of negatively charged DNA towards positively charges surface. The amount of each of the one or more reactants may also be chosen so as to form adsorbents having a desired degree of particle surface coverage by the polymeric material.

Use of Adsorbents

Adsorbent in accordance with the present invention comprise porous inorganic metal oxides surface functionalized with polyelectrolytes. To achieve the adsorption of higher amount of undesirable biological substances, the requirements of the porous molecules are high pore volume (>1.0 cc/g) and high pore size distribution span 90 value (>1.0). If these conditions are met, with the bonding of polyelectrolyte, either positively or negatively charged, the adsorbent materials can be effectively used for use as both adsorbents and clarification agents. In one embodiment, the functionalize adsorbents are used as a bioprocessing clarification agent, wherein the adsorbents comprises: metal oxide particles having a wide pore size distribution as measured by a pore size distribution span 90 value of at least about 1.0; and polymeric material covalently bonded to surfaces of the metal oxide particles.

The absorbent may be used by contacting the functionalized porous adsorbent in a bioprocessing vessel containing undesirable biologics obtained during a bioprocessing procedure; allowing a sufficient incubation time to permit adsorption of the undesirable biologics to the adsorbent or formation of cell pellet and a supernatant layer; separating the resulting mixture through either filtration or decanting or pumping out the supernatant layer and thereafter extracting the desired biological substance from either the filtrates or supernatant or carrying out further purification steps including depth filtration and downstream chromatography steps.

In one embodiment, the adsorbents in accordance with the present invention are added to a bioprocessing vessel containing one or more biomolecules selected from the group consisting of a protein, a polysaccharide, a lipid, a nucleic acid, a metabolites, a mammalian cell, mammalian cell debris, an antibody, a peptide, DNA, RNA, an endotoxin, a virus, a vaccine, an enzyme, or any combination thereof. In other embodiment, the bioprocessing vessel contain at least one of: host cells, cell debris, host cell proteins, nucleic acids, chromatins, antibodies, virus, or vaccines. The functionalized adsorbents bind to one or more biomolecules that come into contact with the adsorbents. Following the binding step in which the adsorbents binds to one or more biomolecules that come into contact with the adsorbents, the adsorbents bound to the one or more biomolecules is separated from other components of the bioprocessing procedure.

It should be understood that although the above-described adsorbents and methods are described as "comprising" one or more components or steps, the above-described adsorbents and methods may "comprise," "consists of," or "consist essentially of" any of the above-described components or steps of the adsorbents and methods. Consequently, where the present invention, or a portion thereof, has been described with an open-ended term such as "comprising," it should be readily understood that (unless otherwise stated) the description of the present invention, or the portion thereof, should also be interpreted to describe the present invention, or a portion thereof, using the terms "consisting essentially of" or "consisting of" or variations thereof as discussed below.

As used herein, the terms "comprises," "comprising," "includes," "including," "has," "having," "contains", "containing," "characterized by" or any other variation thereof, are intended to encompass a non-exclusive inclusion, subject to any limitation explicitly indicated otherwise, of the recited components. For example, an adsorbent and/or method that "comprises" a list of elements (e.g., components or steps) is not necessarily limited to only those elements (or components or steps), but may include other elements (or components or steps) not expressly listed or inherent to the adsorbent and/or method.

As used herein, the transitional phrases "consists of" and "consisting of" exclude any element, step, or component not specified. For example, "consists of" or "consisting of" used in a claim would limit the claim to the components, materials or steps specifically recited in the claim except for impurities ordinarily associated therewith (i.e., impurities within a given component). When the phrase "consists of" or "consisting of" appears in a clause of the body of a claim, rather than immediately following the preamble, the phrase "consists of" or "consisting of" limits only the elements (or components or steps) set forth in that clause; other elements (or components) are not excluded from the claim as a whole.

As used herein, the transitional phrases "consists essentially of" and "consisting essentially of" are used to define a adsorbents and/or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Further, it should be understood that the herein-described adsorbents and/or methods may comprise, consist essentially of, or consist of any of the herein-described components and features, as shown in the figures with or without any feature(s) not shown in the figures. In other words, in some embodiments, the adsorbents and/or methods of the present invention do not have any additional features other than those shown in the figures, and such additional features, not shown in the figures, are specifically excluded from the adsorbents and/or methods. In other embodiments, the adsorbents and/or methods of the present invention do have one or more additional features that are not shown in the figures.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Median particle sizes were determined by laser light scattering using a Malvern Mastersizer 2000, available from Malvern Instrument Ltd. (per ASTM B822-10). Particle size is defined as median particle size by volume distribution. BET surface areas were obtained from the nitrogen sorption analysis described in the literature. Median pore size, pore volume and pore size distribution were calculated based on mercury intrusion into 35-10000 Å size pores. Pore volume is defined as cumulative pore volume in the same pore size range, and median pore size is determined a pore diameter (size) at which 50% pore volume is contributed from smaller pores and 50% pore volume is contributed from bigger pores. Span 90 is defined as a relative pore size span and calculated as (PD90–PD10)/PD50, whereas PD10 is pore diameter at 10% cumulative pore volume contribution and PD50 and PD90 is as defined as 50% and 90% cumulative pore volume contributions based on mercury data, respectively.

1. Polyethyleneimine (PEI) Bonding for Cationic Surface

Six different grades of silica (A, B, C, D, E, F), available from W. R. Grace, were used in the these examples, and their properties (BET Surface Area, Pore Volume, Pore size distribution Span 90, and median pore size PD50) are listed in the Table I below:

TABLE I

| Silica | Surface Area (m²/g) | Pore Volume (cc/g) | Span 90 | PD50 (Å) |
|---|---|---|---|---|
| A | 699 | 1.77 | 7.80 | 432 |
| B | 253 | 1.19 | 2.80 | 154 |
| C | 79 | 1.21 | 1.25 | 500 |
| D | 711 | 0.10 | 0.94 | 90 |
| E | 314 | 0.57 | 1.10 | 569 |
| F | 713 | 0.58 | 0.93 | 104 |
| G | 247 | 0.18 | 0.43 | 50 |
| H | 1 | 0 | 0 | 0 |

The particle size of these silica ranges from 5 μm to 70 μm. Silica B is commercial silica with a Trade name of Syloid® W900, Silica C is a commercial silica with a Trade name of Davisil® XWP 500, Silica F is a commercial silica with a Trade name of Trisyl®. All these are available from W. R. Grace & Co. Silica G is a commercially available (Polyethyleneimine on silica gel, powder, 40-200 mesh from Sigma-Aldrich Corporation) PEI bonded silica sample. Silica H in the Table is a diatomaceous earth (powder, suitable for most filtrations, from Sigma-Aldrich Corporation) and the bonding with PEHA was attempted using the same procedure as the other samples.

Silica A, B had the properties of Pore Volumes of greater than 1.0 cc/g and Span 90 values of greater than 1.0.

In the examples, pentaethylenehexamine (PEHA) was used, a mixture of small molecule polyamines to represent PEI in our examples.

The bonding process consisted of two steps: 1). Surface bonding with epoxy silane (3-glycidoxypropyl-trimethoxysilane), and then 2). Reaction of PEHA with surface epoxy groups (attacking of nucleophilic amino groups to the epoxy ring, and this leads to amine attachment with opening of epoxy ring, forming β-amino alcohols (N. Azizi, M. R. Saidi, Org. Lett., 2005, 7, 3649-3651).

1A. Initial Bonding Procedure

Modified silica samples were prepared by treating the bare silica gel particles (dried in a 120.0° C. oven overnight) with epoxy silane. A 1 L, round bottom indented flask was charged with silica particles (100 g), and then 10 g (10 w/w % to silica) of epoxy silane is added drop-wise into the flask while rotating. The mixture was allowed to roll on a rotovap overnight (16 h). A small portion (2 g) of the sample was separated and washed with 10 ml of acetone five times and dried in a 70° C. oven for 20 hours. The dried sample was subjected to elemental analysis for the amount of carbon content by using a LECO instrument.

1B. PEI Reaction 20 g of bonded silica was weighed from the sample obtained in 1A above and placed in an Erlenmeyer Flask. 6 g of PEHA was weighed in a small beaker (30% w/w to silica), and mixed with 100 g of DIW to dissolve PEHA, to provide ~15% silica slurry for the reaction). The mixture was shaken well and allowed to sit in a water bath (65° C. for 30 min). After the reaction, the silica was further diluted with DI water, filter. Then the silica was soaked with 50 ml 0.5 M HCl for 20-30 minutes and filtered. The resulting silica was washed with DIW for three times (3×100 ml) and dried a small sample at 90° C. overnight. The dried sample was sent for C % analysis. The rest of sample was dried inside the hood in ambient conditions prior to analysis.

1C. Batch Binding Capacity Test

Two model compounds were used in these examples: 1. DNA oligonucleotides (Deoxyribonucleic acid from herring sperm from Sigma-Aldrich), less than 50 base pairs, MW<15000. 2. Bovine serum albumin (BSA) (lyophilized powder, crystallized, ≥98.0% From Sigma), MW ~66000.

Test method: The binding capacities were performed using BSA solution (5 mg/ml) at a pH of 8.0 with 20 mM Tris-HCl buffer, or DNA solution (2 mg/ml) at pH 3.45 with 10 mM sodium phosphate buffer. Dried silica samples were weighed into vials, and then protein solutions (UV/Vis adsorption was measured at 280 nm using a Genesys®10S Bio UV-Vis spectrophotometer). After 2 hr, the supernatants were collected the adsorptions were again measured under the same conditions. The percentage of UV/Vis signal drop were calculated (the higher drop before and after the adsorption, the greater binding capacity). Three parallel adsorption measurements were carried out for one sample and the averages were calculated and reported.

The following table shows the binding capacity results of Examples 1-10:

TABLE 2

| Examples | Silica | C % | DNA Binding | BSA Binding |
|---|---|---|---|---|
| 1 | A | 3.19 | 94% | 33% |
| 2 | B | 1.70 | 77% | 41% |
| 3 | C | 1.25 | 37% | 23% |
| 4 | D | 4.17 | 89% | 0.1% |
| 5 | E | 0.92 | 38% | 5.6% |
| 7 | F | 4.06 | 61% | 1.1% |
| 8 | G | 8.07 | 8.4% | 0.0% |
| 9 | H | 0.05 | 2.0% | 0.0% |
| 10 | A | Unmodified | 20% | 4.1% |

As mentioned above, Examples 1-6 were made by treating the dried silica with epoxysilane and then followed by reacting the silica intermediates with PEHA. The C % numbers, calculated by subtracting the total C % from the C % from the epoxy bonded silica, are indications of the total amount of amines are attached from the reactions. For Sample 7 (commercial PEI-silica) (BET and Hg measurements were carried out after the surface groups of the sample were burnt off by placing samples in an 460° C. muffler oven in air overnight) the binding of DNA and BSA were measured using the same measurement method. The diatomaceous earth (Silica H) for Example 8 was also bonded with PEHA using the same procedure. As shown, Example 8 has very low level of amount of PEHA bonded (due to very low surface area) and the amount of DNA adsorbed.

The results shown above indicate that in order to get high amount of DNA and BSA adsorbed, high pore volume and span 90 are required. Samples 1, 2, and 3 had both pore volume and Span 90 greater than 1.0, and these samples have showed higher binding of both DNA and BSA. Other samples all showed lower binding. In Example 9, due to its high surface area, unbounded silica A had some binding capability of DNA and BAS, but the binding were very low when compared to PEHA bonded Sample 1.

The FIGURE shows the comparison in pore size distributions (from mercury porosimetry) for Silica A and Silica G. As noted, Silica A has the widest pores size distribution ranging from 50 Å to over 5000 Å.

2. Bonding Silica with Anionic Polymers for Binding of Basic Proteins

2A. Preparation

The preparation of anionic polymer bonded silica was achieved by mixing the neutral aqueous solution of polymers (neutralized by base such as ammonium hydroxide or sodium hydroxide) with silica, and then baking the mixture at 190° C. for 5 hrs to force the bonding formation of the polymer and the surface groups. The solutions of commercial poly(acrylic acid) or poly(methacrylic acid) (from Sigma-Aldrich Corporation) were made by dissolving (or diluting if commercial product is an aqueous solution) polymer in DI water and the pH of the solution is adjusted to 7-8 with ammonium hydroxide (or sodium hydroxide). The concentration for the solutions was about 18%.

20 g of silica (Silica A) was mixed with polymer solution containing about 10 g of net polymer. The mixture was placed in a ceramic container and place in an oven in a well ventilated fume hood. The mixture was heated at 90° C. until no liquid is seen, and then baked at 190° C. for 5 hrs. The resulting mixture was re-slurried with DI water, and washed with 5×200 ml of 10% NaCl and 1×200 ml of NaHCO$_3$, followed by 3×100 ml DI water.

2B. Protein Binding Evaluation

The procedure was similar to procedure as described in 1C, with exception that lysozyme (from chicken egg white, lyophilized powder, protein ≥90%, ≥40,000 units/mg protein from Sigma) was used in this test, and the concentration of the protein was 25 mg/ml in 50 mM sodium phosphate, pH 7.0. The amount of adsorbed protein was measured through the amount of signal loss after 2 hr incubation at room temperature, from UV/Vis at 280 nm wavelength, and calculated by lysozyme absorption coefficient.

The following Table 3 shows the protein binding results for Examples 11-14 below:

TABLE 3

| Example # | Polymer | Polymer MW | C % | Lysozyme Binding (mg/mg) |
|---|---|---|---|---|
| 10 | PAA | 100000 | 18.24 | 1.44 |
| 11 | PAA | 240000 | 20.55 | 1.44 |
| 12 | PAA | 15000 | 5.05 | 0.67 |
| 13 | PMA | 9500 | 0.50 | 0.45 |
| 14 | None (Control) | None | 0.00 | 0.52 |

Table 3 shows that higher lysozyme binding is associated with high molecular weight of polymer. Low molecular weight polymer samples had similar binding to that of control, non-polymer bonded silica (Sample 14).

While the invention has been described with a limited number of embodiments, these specific embodiments are not intended to limit the scope of the invention as otherwise described and claimed herein. It may be evident to those of ordinary skill in the art upon review of the exemplary embodiments herein that further modifications, equivalents, and variations are possible. All parts and percentages in the examples, as well as in the remainder of the specification, are by weight unless otherwise specified. Further, any range of numbers recited in the specification or claims, such as that representing a particular set of properties, units of measure, conditions, physical states or percentages, is intended to literally incorporate expressly herein by reference or otherwise, any number falling within such range, including any subset of numbers within any range so recited. For example, whenever a numerical range with a lower limit, $R_L$, and an upper limit $R_U$, is disclosed, any number R falling within the range is specifically disclosed. In particular, the following numbers R within the range are specifically disclosed: $R=R_L+k(R_U-R_L)$, where k is a variable ranging from 1% to 100% with a 1% increment, e.g., k is 1%, 2%, 3%, 4%, 5% . . . 50%, 51%, 52% . . . 95%, 96%, 97%, 98%, 99%, or 100%. Moreover, any numerical range represented by any two values of R, as calculated above is also specifically disclosed. Any modifications of the invention, in addition to those shown and described herein, will become apparent to those skilled in the art from the foregoing description and accompanying drawings. Such modifications are intended to fall within the scope of the appended claims. All publications cited herein are incorporated by reference in their entirety.

What is claimed is:

1. Adsorbents for use as a bioprocessing clarification agent, said adsorbents comprising:
   metal oxide particles having a wide pore size distribution as measured by a pore size distribution span 90 value of greater than 2.5; and
   polymeric material covalently bonded to surfaces of said metal oxide particles.

2. The adsorbents of claim 1, wherein said metal oxide particles have a median particle size of less than about 150 µm.

3. The adsorbents of claim 2, wherein said metal oxide particles have a median pore size of less than about 2000 Å.

4. The adsorbents of claim 3, wherein said metal oxide particles have a pore size distribution of from about 30 to about 5000 Å.

5. The adsorbents of claim 1, wherein said metal oxide particles have a BET particle surface area of at least about 100 m$^2$/g up to about 1000 m$^2$/g.

6. The adsorbents of claim 1, wherein said metal oxide particles have a pore volume, as measured by mercury intrusion, of from about 1.0 ml/g up to about 2.0 ml/g.

7. The adsorbents of claim 1, wherein said metal oxide particles have a pore size distribution span 90 value of about 2.8 to about 7.8.

8. The adsorbents of claim 1, further comprising at least one bifunctional moiety extending from said surfaces of said metal oxide particles, each of said at least one bifunctional moiety comprising (i) one or more functional groups capable of bonding to said surfaces, and either (iia) said polymeric material, or (iib) one or more reactive groups capable of bonding to said polymeric material.

9. The adsorbents of claim 8, wherein said at least one bifunctional moiety comprises an epoxy silane.

10. The adsorbents of claim 9, wherein said at least one bifunctional moiety comprises (3-glycidoxypropyl)-trimethoxysilane.

11. The adsorbents of claim 1, wherein said polymeric material is covalently bonded to said surfaces via a covalent bond linkage consisting of one or more atoms selected from the group consisting of C, O, Si and N.

12. The adsorbents of claim 1, wherein said polymeric material comprises a cationic polyelectrolyte.

13. The adsorbents of claim 12, wherein said cationic polyelectrolyte comprises polyethyleneimine, polyallylamine, polyvinyl pyridine, polydiallyldimethylammonium chloride (pDADMAC), or a copolymer containing one or more cationic or cationic-forming functional groups or the reaction product of said metal oxide particles and an aqueous trimethoxysilyl-polyethyleneimine solution.

14. The adsorbents of claim 13, wherein said cationic polyelectrolyte comprises polyethyleneimine having (i) a weight average molecular weight, Mw, and (ii) a number average molecular weight, Mn, each of which is less than about 5000.

15. The adsorbents of claim 13, wherein said cationic polyelectrolyte comprises polyethyleneimine having a structure:

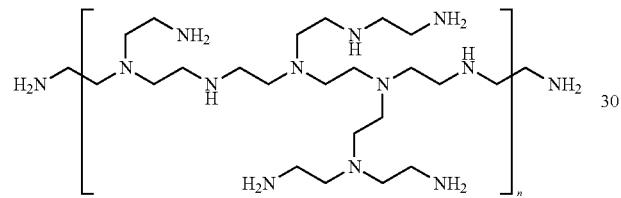

prior to being covalently bonded to said surfaces, and n is a number greater than or equal to 1.

16. The adsorbents of claim 1, wherein said polymeric material comprises an anionic polyelectrolyte.

17. The adsorbents of claim 16, wherein the anionic polyelectrolyte comprises polyacrylic acid, polymethacrylic acid, polystyrene sulfonic acid, nucleic acid, or a copolymer containing one or more anionic or anionic-forming functional groups.

18. The adsorbents of claim 1, wherein said polymeric material is present in an amount representing up to about 20.0 wt % of said adsorbents based on a total weight of said adsorbents.

19. The adsorbents of claim 1, wherein less than 100% of said surfaces are bonded to said polymeric material.

20. The adsorbents of claim 1, wherein said metal oxide particles comprise silica particles.

21. The adsorbents of claim 1, wherein the adsorbents are bound to one or more particular biological compounds, wherein the one or more particular biological compounds comprise a protein, a polysaccharide, a lipid, a nucleic acid, a metabolites, a mammalian cell, mammalian cell debris, an antibody, a peptide, DNA, RNA, an endotoxin, a virus, a vaccine, an enzyme, or any combination thereof.

22. A method of making the adsorbents of claim 1, said method comprising:

contacting the metal oxide particles having a wide pore size distribution as measured by a pore size distribution span 90 value of greater than 2.5 with one or more reactants under reaction conditions that result in the polymeric material covalently bonded to the surfaces of the metal oxide particles, wherein said contacting step utilizes a reaction mixture free of organic solvent.

23. The method of claim 22, wherein the one or more reactants comprise at least one bifunctional compound comprising (i) one or more functional groups capable of bonding the compound to the surfaces of the metal oxide particles, and either (iia) the polymeric material, or (iib) one or more reactive groups capable of bonding to the polymeric material.

24. A method of using adsorbents as defined in claim 1 as a bioprocessing clarification agent, wherein the adsorbents are added to a bioprocessing vessel containing one or more biomolecules, the one or more biomolecules comprising a protein, a polysaccharide, a lipid, a nucleic acid, a metabolites, a mammalian cell, mammalian cell debris, an antibody, a peptide, DNA, RNA, an endotoxin, a virus, a vaccine, an enzyme, or any combination thereof.

25. Adsorbents for use as a bioprocessing clarification agent, said adsorbents comprising:
metal oxide particles having a wide pore size distribution as measured by a pore size distribution span 90 value of greater than 2.0; and
a cationic polyelectrolyte covalently bonded to surfaces of said metal oxide particles, wherein said cationic polyelectrolyte comprises polyethyleneimine, polyallylamine, polyvinyl pyridine, polydiallyldimethylammonium chloride (pDADMAC), or a copolymer containing one or more cationic or cationic-forming functional groups or the reaction product of said metal oxide particles and an aqueous trimethoxysilyl-polyethyleneimine solution.

26. The adsorbents of claim 25, wherein said metal oxide particles comprise silica particles having (i) a wide pore size distribution as measured by a pore size distribution span 90 value of from about 2.8 to about 7.8, (ii) a BET particle surface area of at least about 100 m²/g up to about 1000 m²/g, and (iii) a pore volume, as measured by mercury intrusion, of from about 1.0 ml/g to about 2.0 ml/g.

27. The adsorbents of claim 26, wherein said cationic polyelectrolyte comprises polyethyleneimine.

28. Adsorbents for use as a bioprocessing clarification agent, said adsorbents comprising:
metal oxide particles having a wide pore size distribution as measured by a pore size distribution span 90 value of from about 2.8 to about 7.8; and
polymeric material covalently bonded to surfaces of said metal oxide particles, said polymeric material comprising polyethyleneimine.

29. The adsorbents of claim 28, wherein said metal oxide particles comprise silica particles having (i) a BET particle surface area of at least about 100 m²/g up to about 1000 m²/g, and (ii) a pore volume, as measured by mercury intrusion, of from about 1.0 ml/g to about 2.0 ml/g.

* * * * *